United States Patent
Li et al.

(10) Patent No.: US 9,421,237 B2
(45) Date of Patent: Aug. 23, 2016

(54) TRIPEPTIDE BORONIC ACID OR BORONIC ESTER, PREPARATIVE METHOD AND USE THEREOF

(75) Inventors: Runtao Li, Beijing (CN); Jingrong Cui, Beijing (CN); Yongqiang Zhu, Beijing (CN); Shuyang Yao, Beijing (CN); Zemei Ge, Beijing (CN); Tieming Cheng, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 0 days.

(21) Appl. No.: 13/379,142

(22) PCT Filed: May 17, 2010

(86) PCT No.: PCT/CN2010/072848
§ 371 (c)(1),
(2), (4) Date: Jan. 25, 2012

(87) PCT Pub. No.: WO2010/145376
PCT Pub. Date: Dec. 23, 2010

(65) Prior Publication Data
US 2012/0135921 A1 May 31, 2012

(30) Foreign Application Priority Data
Jun. 19, 2009 (CN) .......................... 2009 1 0147292

(51) Int. Cl.
| | |
|---|---|
| *C07K 5/08* | (2006.01) |
| *C07F 5/02* | (2006.01) |
| *C07F 5/04* | (2006.01) |
| *A61K 31/69* | (2006.01) |
| *A61K 38/06* | (2006.01) |
| *A61P 43/00* | (2006.01) |
| *C07K 5/083* | (2006.01) |
| *C07K 5/087* | (2006.01) |
| *C07K 5/097* | (2006.01) |

(52) U.S. Cl.
CPC ................ *A61K 38/06* (2013.01); *A61K 31/69* (2013.01); *C07F 5/025* (2013.01); *C07K 5/08* (2013.01); *C07K 5/0808* (2013.01); *C07K 5/0812* (2013.01); *C07K 5/0821* (2013.01)

(58) Field of Classification Search
None
See application file for complete search history.

(56) References Cited

U.S. PATENT DOCUMENTS

| | | | | |
|---|---|---|---|---|
| 5,106,948 | A | * 4/1992 | Kinder et al. | 530/331 |
| 5,780,454 | A | 7/1998 | Adams et al. | |
| 6,548,668 | B2 | * 4/2003 | Grenier et al. | 544/69 |
| 2006/0241056 | A1 | * 10/2006 | Orlowski et al. | 514/17 |

FOREIGN PATENT DOCUMENTS

| | | |
|---|---|---|
| WO | 9613266 A1 | 5/1996 |
| WO | 2009006473 A2 | 1/2009 |

OTHER PUBLICATIONS

Zhu, Y., et al., "Design, synthesis and biological evaulation of tripeptide boronic acid proteasome inhibitors," Bioorg. Med. Chem. 17:6851-6861 (2009).*
Paramore and Frantz, "Bortezomib," Nat. Rev. 2:611-612 (2003).*
International Search Report dated Aug. 26, 2010, for corresponding International Application No. PCT/CN2010/072848.
Zhu. Y., et al., "Design, synthesis and biological evaluation of tripeptide boronic acid proteasome inhibitors", Biorganic & Medicinal Chemistry, Aug. 20, 2009, pp. 6851-6861, vol. 17, State Key Laboratory of Natural and Biomimetic Drugs, School of Pharmaceutical Sciences, Peking University, Bejing, China.
Communication pursuant to Rule 114(2) EPC dated Jan. 15, 2014, for corresponding European Patent Application No. 10788772.1.
Communication pursuant to Article 94(3) EPC dated Apr. 3, 2014, for corresponding European Patent Application No. 10788772.1.

* cited by examiner

*Primary Examiner* — Julie Ha
*Assistant Examiner* — Kristina M Hellman
(74) *Attorney, Agent, or Firm* — Pergament & Cepeda LLP; Milagros A. Cepeda; Edward D. Pergament

(57) ABSTRACT

The present invention discloses proteasome inhibitors of tripeptide boronic acids or boronic esters represented by Formula (I), preparative method and use thereof. The proteasome inhibitors are therapeutical agents for treating malignant tumor, various nervous system degenerative diseases, muscle cachexia or diabetes, wherein the malignant tumor is leukemia, gastric cancer, hepatocarcinoma or nasopharyngeal carcinoma.

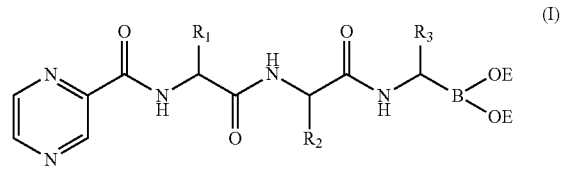

(I)

16 Claims, No Drawings

TRIPEPTIDE BORONIC ACID OR BORONIC ESTER, PREPARATIVE METHOD AND USE THEREOF

This application is a National Stage Application under 35 U.S.C. 371 of PCT International Application No. PCT/CN2010/072848, filed May 17, 2010, which claims priority to Chinese Patent Application No 200910147292.0 filed on June 19, 2009 all of which are hereby incorporate herein by reference in their entireties.

FIELD OF THE INVENTION

The present invention relates to a field of drug production, specifically, the present invention relates to a new kind of tripeptide boronic acid or boronic ester compounds, preparative method and use thereof. Said tripeptide boronic acid or boronic ester compounds have excellent proteasome inhibitory activities, which can be used for treating various genopathies, such as malignant tumor, various nervous system degenerative diseases, muscle cachexia, diabetes and the like.

BACKGROUND OF THE INVENTION

On Oct. 6, 2004, the Royal Swedish Academy of Sciences declared that the Nobel Prize for Chemistry of that year was awarded to Israel scientists Aaron Ciechanover, Avram Hershko and American scientist Irwin Rose for their discovery of protein degradation process regulated by ubiquitin-proteasome passway (hereinafter referred to as "UPP"). It is indicated that the pathway of protein degradation regulated by ubiquitin-proteasome has a tremendous significance in the area of life.

Ubiquitin (Ub for short) is a highly conserved polypeptide chain consisted of 76 amino acids with a molecular weight of 8.5 kD. A lot of molecular biochemical, cellular, genetic and clinical researches indicated that the process of protein degraded by ubiquitin-proteasome was important for regulation of many physiological processes as well as development of various important human diseases. It is discovered recently that this degradation process also has a great impact on pathogenesis of neurodegenerative diseases, Amyotrophic Lateral Sclerosis (ALS), Alzheimer's disease (AD), Parkinson's disease (PD), Huntington's disease (HD), Creutzfeld-Jacob disease (CJD) and diabetes.

It has been well-known that proteasome can modulate the level of protein involved in cell cycle control, such as cyclin acting on G1 phase and mitosis phase, cdk inhibitors, tumor suppressor protein and other regulatory proteins. UPP-dependent protein degradation pathway has been confirmed to play an important role in controlling cell reproduction and cell death, and this pathway also has a great influence on nervous system degenerative diseases such as PD, AD and the like. The use of new inhibitors will reveal more newly unknown functions of ubiquitin proteasome.

Up to date, proteasome inhibitors found can be divided into two kinds, peptides and non-peptides. Peptide inhibitors are usually constituted by short peptides and various pharmacophores attached to the C-terminal thereof, wherein the pharmacophores react with the catalytic amino acid residues of proteasome (primarily hydroxy of threonine in the N-terminal) to form a reversible or irreversible covalent complex, while the remainder of the peptide chain selectively combines with other residues in the subunit active site. At the present time, main pharmacophores include aldehyde groups (peptide aldehydes), vinyl sulfone, boronic acid (peptide boronic acids) and α',β'-epoxy ketone etc.

Compared with peptide aldehyde inhibitors, peptide boronic acid inhibitors have better druggability for the reason that the stability and selectivity of the pharmacophore boronic acid group or boronic ester group of these compounds are better than those of aldehyde group, and that the toxicity of boron substances are very low, and they can finally be degraded into environmentally friendly boronic acid. For example, PS341 (English name is Bortezomib or VELCADE, Chinese name is 硼替佐米, also being called as 万 ), 珂 , which is a dipeptide boronic acid inhibitor, is a novel anti-tumor drug developed by America Millennium Pharmaceuticals, already been marketed in USA, EU and P.R. China. The drug is mainly administered to the patient suffered from multiple myeloma (MM), who have been received at least two or more treatments, and the drug is the only approved proteasome inhibitor currently used in clinical treatment in the world. The drug can overcome the drug resistance of traditional antitumor drugs, so it brings hope for the treatment of multiple myeloma.

U.S. Pat. No. 5,780,454 discloses a new kind of boronic ester compounds P-$AA^1$-$AA^1$-$AA^3$-B($Z^1$)($Z^2$), wherein the compounds include tripeptide boronic ester compounds. However, there are just a few of tripeptide compounds being disclosed, and the structures of said tripeptide compounds are only of two types: L-Leu-L-Leu-L-Leu or L-Leu-L-NaI-L-Leu. The data provided in this patent indicate that the activities of the dipeptide compounds are better than those of the tripeptide compounds.

U.S. Pat. No. 5,693,617 reports tripeptide aldehyde compounds are a type of proteasome inhibitors with high activity. But both the selectivity and stability of these inhibitors are very poor since their pharmacophores are aldehyde groups.

On this basis, the present inventors researched and discovered a new type of tripeptide boronic acid or boronic ester compounds having more desirable proteasome inhibitory activity.

SUMMARY OF THE INVENTION

The objective of the present invention is to provide a new type of tripeptide boronic acid or boronic ester compounds represented by the general Formula (I):

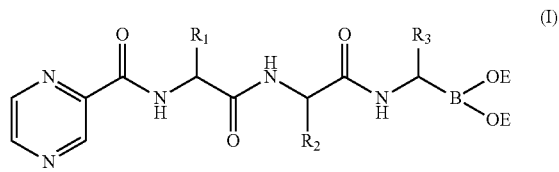

Wherein, $R_1$, $R_2$ and $R_3$ are each independently side chains of L-amino acids, E is H or 2,3-pinanediol ester group, wherein the amino acids are α-amino acids, preferably the amino acids are natural amino acids.

Preferably, $R_1$, $R_2$ and $R_3$ are each independently $C_{1-6}$ linear or branched alkyl, arylmethyl or aromatic heterocyclylmethyl, wherein the aromatic ring of arylmethyl or the aromatic ring of aromatic heterocyclicmethyl can be optionally substituted by the groups selected from $C_{1-4}$ linear or branched alkyl, hydroxyl group, amino group or halogen.

In the definition of the compounds of the present invention, the term "$C_{1-6}$ linear or branched alkyl" refers to linear or branched saturated hydrocarbyl containing 1-6 carbon atoms; preferably linear or branched alkyl containing 3-4 carbon atoms, e.g., propyl, isopropyl, butyl, isobutyl or t-butyl etc.;

more preferably isopropyl, isobutyl or t-butyl; most preferably isobutyl. Similarly, the term "$C_{1-4}$ linear or branched alkyl" used herein refers to linear or branched saturated hydrocarbyl containing 1-4 carbon atoms, such as methyl, ethyl, propyl, isopropyl, isobutyl or t-butyl etc., preferably methyl.

The term "aryl" used herein refers to aromatic groups containing 6-10 carbon atoms, preferably phenyl or naphthyl.

The term "aromatic heterocyclyl" used herein refers to 5- or 6-membered heteroaromatic rings containing one or more heteroatoms selected from N, O and/or S, and the 5- or 6-membered rings can also be fused with benzene ring, and the fused groups are the groups such as pyrrolyl, pyridyl, furyl, thienyl, indyl, benzothienyl, quinolyl or isoquinolyl and the like, more preferably, the aromatic heterocyclyl is indyl.

In the above definition, the aromatic ring of arylmethyl or aromatic heterocyclylmethyl can also be optionally substituted by the groups selected from $C_{1-4}$ linear or branched alkyl, hydroxyl group, amino group or halogen, wherein the term "halogen" refers to fluorine, chlorine, bromine and iodine atom, preferably fluorine, chlorine or iodine atom, and the substituents on the aromatic ring are preferably methyl, hydroxyl group, fluorine or chlorine atom.

Preferably, wherein said $R_1$, $R_2$ and $R_3$ are each independently side chains of L-amino acids, such as benzyl, p-hydroxybenzyl, β-indylmethyl, isobutyl or 2-naphthylmethyl etc, more preferably said $R_3$ group is isobutyl.

According to the above definitions, the three amino acids of the tripeptide moiety in the compounds of the present invention are preferably any combination of the following L-amino acids: leucine, tryptophan, phenylalanine, tyrosine and 2-naphthyl alanine; more preferably, wherein the $R_3$ group is isobutyl, namely, the amino acid closest to the terminal of boronic acid or boronic ester is leucine.

Preferably, the present invention provides the following compounds:
1. Pinanediol N-pyrazineformyl-L-phenylalanyl-L-phenylalanyl-L-leucine borate (5a),
2. Pinanediol N-pyrazineformyl-L-naphthylalanyl-L-phenylalanyl-L-leucine borate (5b),
3. Pinanediol N-pyrazineformyl-L-phenylalanyl-L-tyrosyl-L-leucine borate (5c),
4. Pinanediol N-pyrazineformyl-L-tyrosyl-L-phenylalanyl-L-leucine borate (5d),
5. Pinanediol N-pyrazineformyl-L-leucyl-L-phenylalanyl-L-leucine borate (5e),
6. Pinanediol N-pyrazineformyl-L-leucyl-L-naphthylalanyl-L-leucine borate (5f),
7. Pinanediol N-pyrazineformyl-L-phenylalanyl-L-naphthylalanyl-L-leucine borate (5g),
8. Pinanediol N-pyrazineformyl-L-naphthylalanyl-L-naphthylalanyl-L-leucine borate (5h),
9. Pinanediol N-pyrazineformyl-L-tryptophyl-L-phenylalanyl-L-leucine borate (5i),
10. Pinanediol N-pyrazineformyl-L-phenylalanyl-L-tryptophyl-L-leucine borate (5j),
11. Pinanediol N-pyrazineformyl-L-phenylalanyl-L-leucyl-L-leucine borate (5k),
12. Pinanediol N-pyrazineformyl-L-leucyl-L-leucyl-L-leucine borate (5l),
13. Pinanediol N-pyrazineformyl-L-naphthylalanyl-L-leucyl-L-leucine borate (5m),
14. N-pyrazineformyl-L-phenylalanyl-L-phenylalanyl-L-leucine boronic acid (6a),
15. N-pyrazineformyl-L-naphthylalanyl-L-phenylalanyl-L-leucine boronic acid (6b),
16. N-pyrazineformyl-L-phenylalanyl-L-tyrosyl-L-leucine boronic acid (6c),
17. N-pyrazineformyl-L-tyrosyl-L-phenylalanyl-L-leucine boronic acid (6d),
18. N-pyrazineformyl-L-leucyl-L-phenylalanyl-L-leucine boronic acid (6e),
19. N-pyrazineformyl-L-leucyl-L-naphthylalanyl-L-leucine boronic acid (6f),
20. N-pyrazineformyl-L-phenylalanyl-L-naphthylalanyl-L-leucine boronic acid (6g),
21. N-pyrazineformyl-L-naphthylalanyl-L-naphthylalanyl-L-leucine boronic acid (6h),
22. N-pyrazineformyl-L-tryptophyl-L-phenylalanyl-L-leucine boronic acid (6i),
23. N-pyrazineformyl-L-phenylalanyl-L-tryptophyl-L-leucine boronic acid (6j),
24. N-pyrazineformyl-L-phenylalanyl-L-leucyl-L-leucine boronic acid (6k),
25. N-pyrazineformyl-L-leucyl-L-leucyl-L-leucine boronic acid (6l), and
26. N-pyrazineformyl-L-naphthylalanyl-L-leucyl-L-leucine boronic acid (6m).

Wherein the serial numbers in the brackets are the serial numbers used for the description of the compounds in the present invention.

Another objective of the present invention is to provide a preparation method for the above-mentioned compound represented by the above general formula, and this method comprises the following steps: using pyrazinecarboxylic acid as a starting raw material, introducing the required two amino acids one by one, and then introducing the boronic ester of the required third amino acid to give the boronic ester of the above general formula (I) of the present invention; if the corresponding boronic acid was needed to be prepared, the preparation can be carried out by hydrolyzing the above-mentioned boronic ester of the above general formula (I).

Wherein, the general formula compounds in which the $R_3$ group is isobutyl, namely, the amino acid closest to the terminal of boronic acid or boronic ester is leucine, can be prepared according to the following synthetic route by using pyrazinecarboxylic acid as the starting raw material:

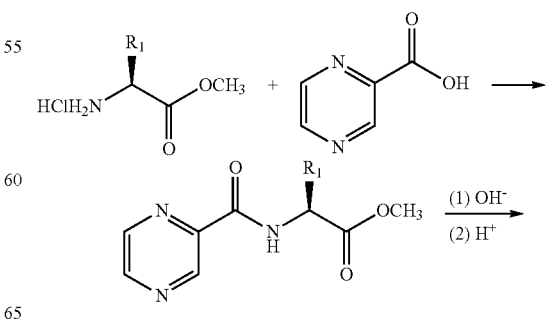

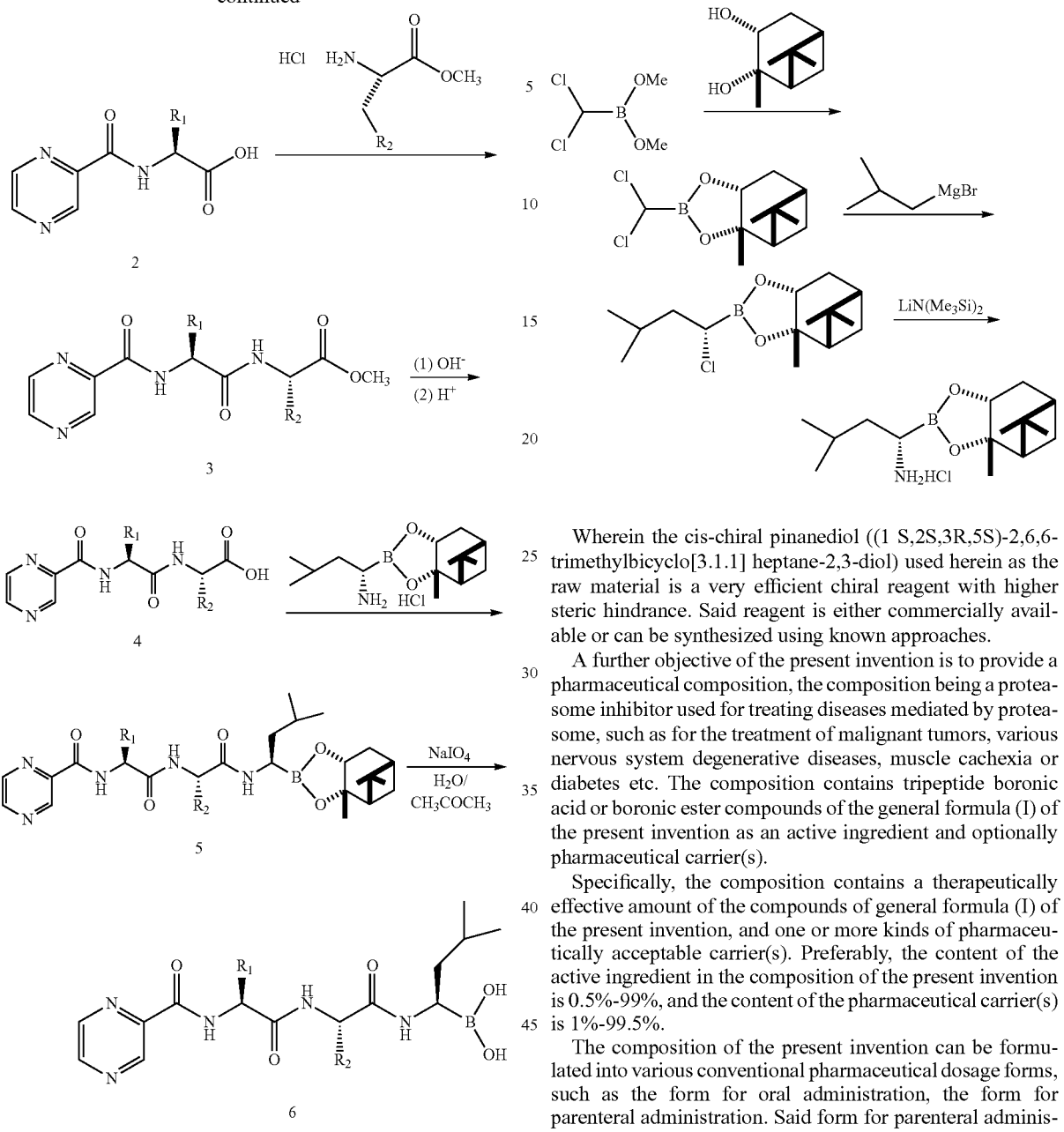

The above method mainly comprises steps of introducing amino acids one by one, each step of introducing amino acids comprises pyrazinecarboxylic acid reacting with the methyl esters of the amino acids firstly, then hydrolyzing the obtained compounds to give the corresponding amino acids, the processes of introducing amino acids can be carried out according to the routine methods used in the peptide synthesis.

Wherein the leucine borate used as the raw material (LeuB-diol-NH$_2$ for short in the present context) can be prepared according to the method disclosed in the literature (Hall, D. G., Structure, properties, and preparation of boronic acid derivatives, WILEY-VCH Verlag GmbH & Co. KgaA, Weinheim. 2005, p8) or can be prepared according to the following synthetic route:

Wherein the cis-chiral pinanediol ((1 S,2S,3R,5S)-2,6,6-trimethylbicyclo[3.1.1] heptane-2,3-diol) used herein as the raw material is a very efficient chiral reagent with higher steric hindrance. Said reagent is either commercially available or can be synthesized using known approaches.

A further objective of the present invention is to provide a pharmaceutical composition, the composition being a proteasome inhibitor used for treating diseases mediated by proteasome, such as for the treatment of malignant tumors, various nervous system degenerative diseases, muscle cachexia or diabetes etc. The composition contains tripeptide boronic acid or boronic ester compounds of the general formula (I) of the present invention as an active ingredient and optionally pharmaceutical carrier(s).

Specifically, the composition contains a therapeutically effective amount of the compounds of general formula (I) of the present invention, and one or more kinds of pharmaceutically acceptable carrier(s). Preferably, the content of the active ingredient in the composition of the present invention is 0.5%-99%, and the content of the pharmaceutical carrier(s) is 1%-99.5%.

The composition of the present invention can be formulated into various conventional pharmaceutical dosage forms, such as the form for oral administration, the form for parenteral administration. Said form for parenteral administration is various forms suitable for injection administration, topical administration, inhalation administration, rectal administration or implantable administration. Preferably the form is suitable for injection administration, such as injections, freeze-dried powder injections or infusion solutions; or the form is suitable for oral administration, such as tablets, capsules, granules or other liquid preparations suitable for oral administration such as solutions, emulsions, suspensions etc. Preferably the oral preparation is tablets which can be formulated into coated or enteric-coated form, preferably the oral preparation can be formulated into sustained-release or quantitative release form.

For preparing suitable dosage form, one or more kinds of pharmaceutical carrier(s) as required can be added into the active ingredient, said pharmaceutical carriers include various routine pharmaceutical adjuvants, such as excipients, fillers, diluents, disintegrants, surfactants, wetting agents, preservatives, sweetening agents and pigment etc.

According to the type and the severity of diseases, and the conditions of patients such as sex, age, body weight (bw) etc., appropriate preparation and applied dosage are selected, generally, the applied dosage for an adult is 1-200 mg/kg bw/day, preferably 1-50 mg/kg bw/day.

The pharmaceutical composition of the present invention and various dosage forms thereof can be prepared according to the routine approaches well known in the pharmaceutical area using routine pharmaceutical carriers.

The tripeptide boronic acid or boronic ester compounds of the present invention have favorable inhibitory activity on proteasome that can be used as a new proteasome inhibitor for treating diseases such as malignant tumors, various nervous system degenerative diseases, muscle cachexia or diabetes and the like.

Another objective of the present invention is to provide a pharmaceutical use of the compounds of the general formula (I) and the pharmaceutical composition containing such compounds. Namely, the present invention provides the use of the compounds of the general formula (I) and the pharmaceutical composition containing aforesaid compounds for the preparation of proteasome inhibitor, especially the use of the compounds or the pharmaceutical composition in the preparation of medicament for treating diseases such as malignant tumors, various nervous system degenerative diseases, muscle cachexia or diabetes and the like. The diseases include various malignant tumors, neurodegenerative diseases, amyotrophic lateral sclerosis, Alzheimer's disease, Parkinson's disease, Huntington's Chorea, Creutzfeldt-Jakob disease and diabetes, wherein said malignant tumor is leukaemia, gastric cancer, hepatocarcinoma or nasopharyngeal carcinoma.

Another objective of the present invention is to provide a method for treating various malignant tumors, neurodegenerative diseases, amyotrophic lateral sclerosis, Alzheimer's disease, Parkinson's disease, Huntington's Chorea, Creutzfeldt-Jakob disease or diabetes, the method including administering a therapeutically-effective amount of the compounds of general formula (I) to a patient in need thereof; wherein said malignant tumor is leukaemia, gastric cancer, hepatocarcinoma or nasopharyngeal carcinoma etc.

It has been proved that tripeptide boronic acid or boronic ester of the present invention has favorable inhibitory activity on proteasome, the antitumor activity is better than that of the known drug bortezomib, thus the tripeptide boronic acid or boronic ester can be used in place of bortezomib for treating malignant tumors, especially for treating multiple myeloma. In the experiments on the test models of HL-60 human leukaemia, BGC-823 human gastric cancer, Bel-7402 human hepatocarcinoma and KB human nasopharyngeal carcinoma, the compounds of the present invention exhibit favorable activity.

SPECIFIC EMBODIMENTS OF THE INVENTION

The following specific embodiments are used for further illustration of the technical solutions of the present invention, wherein the examples listed are only intended to illustrate the present invention, instead of limiting the protection scope of the present invention in any way.

PREPARATION EXAMPLE 1

L-phenylalanine Methyl Ester Hydrochloride

To a 100 ml of reaction flask was added 25 ml of absolute methanol, then cooled down to −10° C. or below using an ice-salt bath, and $SOCl_2$ (7 ml, 96 mmol) was added dropwise slowly under stirring, then reacted for 10 min at a temperature of −10° C. or below, followed by addition of L-phenylalanine (1.65 g, 10 mmol), reacted at a low temperature for 40 min, the ice-salt bath was removed, the obtained solution reacted for 48 h at room temperature, and concentrated under reduced pressure, 15 ml of methanol was added, the result solution was concentrated under reduced pressure for twice. 50 ml of diethyl ether was added, standing, needle crystal was precipitated, filtered and dried, the obtained crude product was recrystallized from methanol-diethyl ether, 2.0 g of white crystal of L-phenylalanine methyl ester hydrochloride was given with a yield of 95%, $[\alpha]_D^{25}$=+37.2° (c=1, $CH_3CH_2OH$), m.p.: 155-158° C.

PREPARATION EXAMPLE 2

N-pyrazineformyl-L-phenylalanine Methyl Ester

The product L-phenylalanine methyl ester hydrochloride of Preparation example 1 (1.12 g, 5.2 mmol) was dissolved in 20 ml of THF, and neutralized with N-methyl morpholine (NMM) (0.7 ml, 6.2 mmol), then cooled with an ice bath for later use. Pyrazinecarboxylic acid (0.65 g, 5.2 mmol) was added to another reaction flask, dissolved with 20 ml of THF, cooled with an ice water bath, dicyclohexylcarbodiimide (DCC) (1.07 g, 5.2 mmol) and HOBt (0.84 g, 6.2 mmol) were added at 0° C. and reacted for 40 min at 0° C., to which the solution of L-phenylalanine methyl ester hydrochloride in THF prepared, cooled and neutralized according to the above was added, the reaction was monitored by TLC and completed after 2 h, insoluble N,N'-dicyclohexylurea (DCU) was removed by filtration, to the filtrate was added 150 ml of ethyl acetate, washed with 5% sodium bicarbonate solution, 10% citric acid solution, 5% sodium bicarbonate solution, saturated salt solution (2×20 ml) successively. The ethyl acetate layer was dried over anhydrous sodium sulfate, filtered, and evaporated the solvent under reduced pressure, 1.37 g of white solid was obtained with a yield of 98%, m.p.: 152-155° C. $^1$H-NMR ($CDCl_3$, 300 MHz): δ 3.26 (—$CH_2$, m, 2H), 3.75 (—$CH_3$, s, 3H), 5.09 (—CH, m, 1H), 7.15~7.32 (-Ph, m, 5H), 8.23 (—CONH, d, 1H), 8.52 (-Pyz, d, 1H), 8.74 (-Pyz, d, 1H), 9.37 (-Pyz, s, 1H).

PREPARATION EXAMPLE 3

N-pyrazineformyl-L-phenylalanine

The product N-pyrazineformyl-L-phenylalanine methyl ester (1.0 g, 3.51 mmol) in Preparation example 2 was dissolved with 10 ml of acetone, 2N NaOH was added dropwise slowly until a pH value of 12~13 was obtained, and the solution was kept reacting under the condition of ice water bath, the reaction was monitored by TLC and completed after 2 h. Hydrochloric acid was add dropwise under the condition of ice water bath until a pH value of 2~3 was obtained, a large amount of white solid was produced, the generated precipitate was filtered, washed with water and diethyl ether followed by airing to dry and gave 0.89 g of white product with a yield of 93.6%, m.p.: 166-169° C. $^1$H-NMR (DMSO-$d_6$, 300 MHz): δ 3.23 (—$CH_2$, m, 2H), 4.74 (—CH, m, 1H), 7.16~7.25 (-Ph, m, 5H), 8.74 (—CONH, t, 1H), 8.86~8.89 (-Pyz, t, 2H), 9.14 (-Pyz, d, 1H), 13.06 (—COOH, s, 1H).

PREPARATION EXAMPLE 4

N-pyrazineformyl-L-phenylalanyl-L-phenylalanine Methyl Ester

L-phenylalanine methyl ester hydrochloride (0.8 g, 3.69 mmol) was dissolved with 20 ml of THF, then the hydrochloric acid was neutralized with NMM (0.49 ml, 4.43 mmol), cooled with an ice bath for later use. N-Pyrazineformyl-L-phenylalanine (1.0 g, 3.69 mmol) of Preparation example 3 was added to another reaction flask, dissolved with 20 ml of THF, and cooled with an ice water bath, dicyclohexylcarbodiimide (DCC) (0.76 g, 3.69 mmol), HOBt (0.60 g, 4.42 mmol) were added at 0° C. and reacted for 40 min at 0° C., then the solution of L-phenylalanine methyl ester hydrochloride in THF prepared, cooled and neutralized according to the above was added, the reaction was monitored by TLC and completed after 2 h, insoluble DCU was removed by filtration, to the filtrate was added 80 ml of ethyl acetate, washed with 5% sodium bicarbonate solution, 10% citric acid solution, 5% sodium bicarbonate solution, saturated salt solution (2×20 ml) successively. The ethyl acetate layer was dried over anhydrous sodium sulfate, filtered, and evaporated the solvent under reduced pressure, 1.52 g of white solid was obtained with a yield of 95.6%, m.p.: 111~113° C. $^1$H-NMR (CDCl$_3$, 300 MHz): δ 3.04 (—CH$_2$, m, 2H), 3.18 (—CH$_2$, d, 2H), 3.69 (—CH$_3$, s, 3H), 4.82 (—CH, m, 2H), 6.36 (—CONH, d, 1H), 6.92~7.30 (-Ph, m, 10H), 8.26 (—CONH, d, 1H), 8.54 (-Pyz, d, 1H), 8.76 (-Pyz, d, 1H), 9.33 (-Pyz, s, 1H).

PREPARATION EXAMPLE 5

N-pyrazineformyl-L-phenylalanyl-L-phenylalanine

The product of N-pyrazineformyl-L-phenylalanyl-L-phenylalanine methyl ester (1.52 g, 3.52 mmol) in Preparation example 4 was dissolved with 10 ml of acetone, 2N NaOH was added dropwise slowly under the condition of ice water bath until a pH value of 12~13 was obtained, and the solution was kept reacting under the condition of an ice water bath, the reaction was monitored by TLC and completed after 2 h. Hydrochloric acid was added dropwise under the condition of ice water bath until a pH value of 2~3 was obtained, a large amount of white solid was produced, the generated precipitate was filtered, washed with diethyl ether followed by airing to dry, 1.33 g of white product was obtained with a yield of 90.5%, the melting point of the white solid: 194-196° C.; $^1$H-NMR (DMSO-d$_6$, 300 MHz): δ 12.88 (s, 1H), 9.10 (s, 1H), 8.90-8.87 (m, 1H), 8.77-8.73 (m, 1H), 8.75-8.65 (m, 2H), 7.24-7.14 (m, 10H), 4.84-4.80 (m, 1H), 4.53-4.50 (m, 1H), 3.14-2.89 (m, 4H).

PREPARATION EXAMPLE 6

N-pyrazineformyl-L-naphthylalanine

Using naphthylalanine methyl ester hydrochloride as a raw material, the synthesis and work-up procedures were similar with that described in Preparation example 3. 2.96 g of reddish-brown sticky solid was obtained with a yield of 97.4%. $^1$H-NMR (DMSO-d$_6$, 300 MHz): δ 4.78 (—CH, s, 1H), 6.92~7.54 (=CH, m, 5H), 8.74 (—CONH, -Pyz, d, 2H), 8.87 (-Pyz, s, 1H), 9.15 (-Pyz, s, 1H), 10.86 (—NH, s, 1H), 13.04 (—COOH, s, 1H).

PREPARATION EXAMPLE 7

N-pyrazineformyl-L-naphthylalanyl-L-phenylalanine Methyl Ester

Using the product of N-pyrazineformyl-L-naphthylalanine in Preparation example 6 as a raw material, the synthetic approach and work-up were analogous to that described in Preparation example 4. 1.89 g of yellow sticky substance was obtained with a yield of 94.2%. The product was directly used for the next step of saponification.

PREPARATION EXAMPLE 8

N-pyrazineformyl-L-naphthylalanyl-L-phenylalanine

Using the product 2b of Preparation example 7 as a raw material, the synthetic approach and work-up were analogous to that described in Preparation example 5. The yield was 77%, white solid, m.p.: 196-197° C.; $^1$H-NMR (DMSO-d$_6$, 300 MHz): δ 9.07 (s, 1H), 8.86 (d, J=2.7 Hz, 1H), 8.70 (d, J=1.2 Hz, 1H), 8.68-8.62 (m, 2H), 7.83-7.72 (m, 4H), 7.45-7.37 (m, 3H), 7.24-7.17 (m, 5H), 4.93-4.91 (m, 1H), 4.53-4.50 (m, 1H), 3.24-2.98 (m, 4H).

PREPARATION EXAMPLE 9

N-pyrazineformyl-L-phenylalanyl-L-tyrosine Methyl Ester

Using the product of Preparation example 3 and tyrosine methyl ester hydrochloride as raw materials, the synthetic approach and work-up were analogous to that described in Preparation example 4. A yellow sticky substance was obtained with a yield of 92%. The product was directly used for the next step of saponification.

PREPARATION EXAMPLE 10

N-pyrazineformyl-L-phenylalanyl-L-tyrosine

Using the product 2c of Preparation example 9 as raw materials, the synthetic approach and work-up were analogous to that described in Preparation example 5. A spumescence solid was obtained with a yield of 83% and the product was directly used for the next reaction.

PREPARATION EXAMPLE 11

N-pyrazineformyl-L-tyrosine

Using N-pyrazinecarboxylic acid and tyrosine methyl ester hydrochloride as raw materials, the synthetic approach was analogous to that described in Preparation example 3, a milk-white sticky solid was obtained with a yield of 89%, and the product was directly used for the next reaction.

PREPARATION EXAMPLE 12

N-pyrazineformyl-L-tyrosyl-L-phenylalanine Methyl Ester

Using the product of Preparation example 11 as a raw material, the synthetic method and work-up were analogous to that described in Preparation example 4. 2.26 g of yellow viscous substance was obtained with a yield of 95.5% and the product was directly used for the next step of saponification.

PREPARATION EXAMPLE 13

N-pyrazineformyl-L-tyrosyl-L-phenylalanine

Using the product of Preparation example 12 as a raw material, the synthetic approach and work-up were analogous to that described in Preparation example 5. A spumescence solid was obtained with a yield of 86% and the product was directly used for the next reaction.

PREPARATION EXAMPLE 14

L-leucine Methyl Ester Hydrochloride

Using L-leucine as a raw material, the synthetic approach and work-up were analogous to that described in Preparation example 1. 1.7 g of white crystal was obtained with a yield of 94%, $[\alpha]D^{25}=+20.2°$ (c=1, $CH_3OH$), m.p.: 149-150° C.

PREPARATION EXAMPLE 15

N-pyrazineformyl-L-leucine Methyl Ester

Using the product of Preparation example 14 as a raw material, the synthetic approach and work-up were analogous to that described in Preparation example 2. 2.47 g of red sticky liquid was obtained with a yield of 98%. $^1$H-NMR ($CDCl_3$, 300 MHz): δ 0.97~0.99 (—$CH_3$, m, 6H), 1.69~1.83 (—$CH_2$, —CH, m, 3H), 3.78 (—$CH_3$, s, 3H), 4.82~4.90 (—CH, m, 1H), 8.15 (—CONH, d, 1H), 8.57 (-Pyz, q, 1H), 8.78 (-Pyz, d, 1H), 9.40 (-Pyz, s, 1H).

PREPARATION EXAMPLE 16

N-pyrazineformyl-L-leucine

Using the product of N-pyrazineformyl-L-leucine methyl ester in Preparation example 15 as a raw material, the synthetic approach and work-up were analogous to that described in Preparation example 3. 2.22 g of white solid was obtained with a yield of 95%, m.p.: 36-38° C. $^1$H-NMR (DMSO-$d_6$, 300 MHz): δ 0.88~0.91 (—$CH_3$, t, 6H), 1.57~1.64 (—$CH_2$, m, 2H), 1.81~1.91 (—CH, m, 1H), 4.48~4.55 (—CH, m, 1H), 8.77 (—CONH, q, 1H), 8.90~8.95 (-Pyz, dd, 2H), 9.19 (-Pyz, d, 1H), 12.81 (—COOH, s, 1H).

PREPARATION EXAMPLE 17

N-pyrazineformyl-L-leucyl-L-phenylalanine Methyl Ester

Using the product of N-pyrazineformyl-L-leucine in preparation example 16 as a raw material, the synthetic approach and work-up were analogous to that described in Preparation example 4. The product was a yellow sticky substance with a yield of 93%. $^1$H-NMR ($CDCl_3$, 300 MHz): δ 0.92~0.96 (—$CH_3$, dd, 6H), 1.64~1.79 (—$CH_2$, —CH, m, 3H), 3.02~3.20 (—$CH_2$, m, 2H), 3.74 (—$CH_3$, s, 3H), 4.64 (—CH, m, 1H), 4.88 (—CH, dd, 1H), 6.64 (—CONH, d, 1H), 7.03~7.10 (-Ph, m, 5H), 8.03 (—CONH, d, 1H), 8.55 (-Pyz, q, 1H), 8.79 (-Pyz, d, 1H), 9.36 (-Pyz, d, 1H).

PREPARATION EXAMPLE 18

N-pyrazineformyl-L-leucyl-L-phenylalanine

Using the product 2e of Preparation example 17 as a raw material, the synthetic approach and work-up were analogous to that described in Preparation example 18. A sticky solid was obtained with a yield of 95.6%; $^1$H-NMR (DMSO-$d_6$, 300 MHz): δ 12.61 (s, 1H), 9.20 (s, 1H), 8.98-8.91 (m, 1H), 8.77 (s, 1H), 8.66-8.62 (m, 1H), 8.46-8.44 (m, 1H), 7.22-7.15 (m, 5H), 4.61 (s, 1H), 4.48-4.46 (m, 1H), 3.10-2.87 (m, 2H), 1.98-1.92 (m, 1H), 1.62-1.59 (m, 2H), 0.92-0.88 (m, 6H).

PREPARATION EXAMPLE 19

N-pyrazineformyl-L-leucyl-L-naphthylalanine Methyl Ester

Using the product of N-pyrazineformyl-L-leucine in Preparation example 16 as a raw material, the synthetic approach and work-up were analogous to that described in Preparation example 4. 2.1 g of yellow sticky substance was obtained with a yield of 93%. The product was directly used for the next step of saponification.

PREPARATION EXAMPLE 20

N-pyrazineformyl-L-leucyl-L-naphthylalanine

Using the product of Preparation example 19 as a raw material, the synthetic approach and work-up were analogous to that described in Preparation example 5. A white solid was obtained with a yield of 83%, m.p.: 99-100° C.; $^1$H-NMR (DMSO-$d_6$, 300 MHz): δ 9.16 (s, 1H), 8.89 (d, J=2.4 Hz, 1H), 8.70 (d, J=1.5 Hz, 1H), 8.58 (d, J=9.0 Hz, 1H), 8.46 (d, J=7.8 Hz, 1H), 7.79-7.73 (m, 4H), 4.60-4.57 (m, 1H), 4.55-4.53 (m, 1H), 1.54-1.45 (m, 3H), 0.83-0.79 (m, 6H).

PREPARATION EXAMPLE 21

N-pyrazineformyl-L-phenylalanyl-L-naphthylalanine Methyl Ester

Using the product of Preparation example 3 as a raw material, the synthetic approach and work-up were analogous to that described in Preparation example 4. 2.3 g of yellow sticky substance was obtained with a yield of 93.5%. The product was directly used for the next reaction.

PREPARATION EXAMPLE 22

N-pyrazineformyl-L-phenylalanyl-L-naphthylalanine

Using the product of Preparation example 21 as a raw material, the synthetic approach and work-up were analogous to that described in Preparation example 5. A white solid was obtained with a yield of 79%, m.p.: 191-193° C.; $^1$H-NMR (DMSO-$d_6$, 300 MHz): δ 9.07 (d, J=1.2 Hz, 1H), 8.86 (d, J=2.7 Hz, 1H), 8.68 (d, J=1.5 Hz, 1H), 8.64-8.56 (m, 2H), 7.81-7.72 (m, 4H), 7.42-7.40 (m, 3H), 7.17-7.11 (m, 5H), 4.83-4.79 (m, 1H), 4.59-4.55 (m, 1H), 3.26-3.02 (m, 4H).

PREPARATION EXAMPLE 23

N-pyrazineformyl-L-naphthylalanyl-L-naphthylalanine Methyl Ester

Using the product of Preparation example 6 as a raw material, the synthetic approach and work-up were analogous to that described in Preparation example 4. 1.89 g of yellow sticky substance was obtained with a yield of 94.2%. The product was directly used for the next step of saponification.

PREPARATION EXAMPLE 24

N-pyrazineformyl-L-naphthylalanyl-L-naphthylalanine

Using the product of Preparation example 23 as a raw material, the synthetic approach and work-up were analogous to that described in Preparation example 5. Light yellow solid was obtained with a yield of 72%, m.p.: 208-209° C.; $^1$H-NMR (DMSO-$d_6$, 300 MHz): δ 9.04 (s, 1H), 8.84 (d, J=2.4 Hz, 1H), 8.73-8.69 (m, 1H), 8.67-8.66 (m, 2H), 7.82-7.69 (m, 8H), 7.74-7.69 (m, 6H), 7.44-7.35 (m, 6H), 4.95-4.91 (m, 1H), 4.64-4.60 (m, 1H), 3.28-3.08 (m, H).

PREPARATION EXAMPLE 25

L-tryptophan Methyl Ester Hydrochloride

Using L-tryptophan as a raw material, the synthetic approach and work-up were analogous to that described in Preparation example 1. 3.02 g of white crystal was obtained with a yield of 93%, $[α]D^{25}$=+16.5° (c=1, $CH_3OH$), m.p.: 206-208° C.

PREPARATION EXAMPLE 26

N-pyrazineformyl-L-tryptophan Methyl Ester

Using N-pyrazinecarboxylic acid and the product of Preparation example 25 as a raw material, the synthetic approach and work-up were analogous to that described in Preparation example 2. 3.18 g of reddish-brown sticky substance was obtained with a yield of 96%, and the product was directly used for the next reaction.

PREPARATION EXAMPLE 27

N-pyrazineformyl-L-tryptophan

Using the product of Preparation example 26 as a raw material, the synthetic approach and work-up were analogous to that described in Preparation example 3. 2.96 g of reddish-brown sticky solid was obtained with a yield of 97.4%. $^1$H-NMR (DMSO-$d_6$, 300 MHz): δ 4.78 (—CH, s, 1H), 6.92~7.54 (=CH, m, 5H), 8.74 (—CONH, -Pyz, d, 2H), 8.87 (-Pyz, s, 1H), 9.15 (-Pyz, s, 1H), 10.86 (—NH, s, 1H), 13.04 (—COOH, s, 1H).

PREPARATION EXAMPLE 28

N-pyrazineformyl-L-tryptophyl-L-phenylalanine Methyl Ester

Using the product of Preparation example 27 as a raw material, the synthetic approach and work-up were analogous to that described in Preparation example 4. 2.13 g of yellow sticky substance was obtained with a yield of 96.8%, and the product was directly used for saponification without separation.

PREPARATION EXAMPLE 29

N-pyrazineformyl-L-tryptophyl-L-phenylalanine

Using the product of Preparation example 28 as a raw material, the synthetic approach and work-up were analogous to that described in Preparation example 3. The yield was 96.4%, white solid, m.p.: 74-76° C.; $^1$H-NMR (DMSO-$d_6$, 300 MHz): δ 10.79 (s, 1H), 9.13 (s, 1H), 8.86 (s, 1H), 8.68 (s, 1H), 8.62-8.59 (m, 2H), 7.54-6.84 (m, 10H), 4.84 (s, 1H), 4.58-4.50 (m, 2H), 3.20-3.09 (m, 4H).

PREPARATION EXAMPLE 30

N-pyrazineformyl-L-phenylalanyl-L-tryptophan Methyl Ester

Using the product of Preparation example 3 as a raw material, the synthetic approach and work-up were analogous to that described in Preparation example 4. 1.65 g of light yellow oily liquid was obtained with a yield of 94.8%. $^1$H-NMR ($CDCl_3$, 300 MHz): δ 3.13~3.24 (—$CH_2$, m, 4H), 3.68 (—$CH_3$, s, 3H), 4.90 (—CH, q, 1H), 5.06 (—CH, m, 1H), 6.79 (—NH, s, 1H), 6.91~7.34 (-Ph, =CH, m, 10H), 8.26~8.33 (—CONH, t, 2H), 8.43 (-Pyz, d, 1H), 8.63 (-Pyz, d, 1H), 9.14 (-Pyz, s, 1H).

PREPARATION EXAMPLE 31

N-pyrazineformyl-L-phenylalanyl-L-tryptophan

Using the product of Preparation example 30 as a raw material, the synthetic approach and work-up were analogous to that described in Preparation example 5. A light yellow solid was obtained with a yield of 93.7%, m.p.: 106-108° C.; $^1$H-NMR (DMSO-$d_6$, 300 MHz): δ 12.59 (s, 1H), 10.87 (s, 1H), 9.16-9.12 (m, 1H), 8.89-8.87 (m, 1H), 8.75-8.72 (m, 1H), 8.66-8.59 (m, 2H), 7.56-6.96 (m, 10H), 4.88-4.85 (m, 1H), 4.59-4.56 (m, 1H), 3.22-3.05 (m, 4H).

PREPARATION EXAMPLE 32

N-pyrazineformyl-L-phenylalanyl-L-leucine Methyl Ester

Using the product of Preparation example 3 as a raw material, the synthetic approach and work-up were analogous to that described in Preparation example 4. 1.20 g of white sticky solid was obtained with a yield of 94.5%, and the product was directly used for the next step of saponification.

PREPARATION EXAMPLE 33

N-pyrazineformyl-L-phenylalanyl-L-leucine

Using the product of Preparation example 32 as a raw material, the synthetic approach and work-up were analogous to that described in Preparation example 5. The yield was 93.9%, light yellow solid, m.p.: 142-144° C.; $^1$H-NMR (DMSO-$d_6$, 300 MHz): δ 12.70 (s, 1H), 9.15-9.12 (m, 1H), 8.90-8.88 (m, 1H), 8.79-8.74 (m, 1H), 8.68-8.65 (m, 1H), 8.57-8.53 (m, 1H), 7.27-7.15 (m, 5H), 4.90-4.82 (m, 1H), 4.32-4.25 (m, 1H), 3.21-3.04 (m, 2H), 1.68-1.54 (m, 3H), 0.94-0.91 (m, 3H), 0.87-0.85 (m, 3H).

PREPARATION EXAMPLE 34

N-pyrazineformyl-L-leucyl-L-leucine Methyl Ester

Using the product N-pyrazineformyl-L-leucine in Preparation example 16 as a raw material, the synthetic approach and work-up were analogous to that described in Preparation example 4. 1.69 g of yellow sticky substance was obtained with a yield of 91.8%. The product was directly used for the next step of saponification.

PREPARATION EXAMPLE 35

N-pyrazineformyl-L-leucyl-L-leucine

Using the product of Preparation example 34 as a raw material, the synthetic approach and work-up were analogous to that described in Preparation example 5. A sticky solid was obtained with a yield of 83%, the product was directly used for the next reaction.

PREPARATION EXAMPLE 36

N-pyrazineformyl-L-naphthylalanyl-L-leucine Methyl Ester

Using the product of Preparation example 6 as a raw material, the synthetic approach and work-up were analogous to that described in Preparation example 4. 1.8 g of yellow sticky substance was obtained with a yield of 92.5%. The product was directly used for the next step of saponification.

PREPARATION EXAMPLE 37

N-pyrazineformyl-L-naphthylalanyl-L-leucine

Using the product of Preparation example 36 as a raw material, the synthetic approach and work-up were analogous to that described in Preparation example 5. A white solid was obtained with a yield of 78%, m.p.: 98-100° C.; $^1$H-NMR (DMSO-$d_6$, 300 MHz): δ 9.09 (d, J=1.2 Hz, 1H), 8.86 (d, J=2.7 Hz, 1H), 8.71-8.70 (m, 2H), 8.57 (d, J=7.8 Hz, 1H), 7.84-7.45 (m, 4H), 7.43-7.42 (m, 3H), 5.02-4.96 (m, 1H), 4.32-4.28 (m, 1H), 1.66-1.58 (m, 3H), 0.89 (d, J=6.6 Hz, 3H), 0.83 (d, J=6.3 Hz, 3H).

PREPARATION EXAMPLE 38

(1S,2S,3R,5S)-2,6,6-trimethylbicyclo[3.1.1]heptane-2,3-diol

Me$_3$NO.2H$_2$O (11.3 g, 102 mmol) was dissolved with 16 ml of water, α-pinene (13.2 g, 96.9 mmol), 74 ml of tert-butyl alcohol, 7.4 ml of pyridine and osmium tetroxide (60 mg, 0.236 mmol) were added under stirring. Then nitrogen gas was purged, 10 min later, the reaction mixture was heated to reflux. The reaction was monitored by TLC and finished after 15 h. Spontaneously cooled down to room temperature, NaHSO$_3$ (1.2 g, 11.5 mmol) and an appropriate amount of saturated aqueous NaCl solution were added. The organic phase was separated out, and the water layer was extracted with diethyl ether (3×20 ml), the organic phase was combined and dried over anhydrous sodium sulfate. The product was concentrated and the residue was purified by column chromatography (ethyl acetate:petroleum ether=1:30), 15.33 g of white solid was obtained, and the yield was 92.9%, [α]$D^{20}$=−10.79° (c=5.5, toluene), m.p.: 52-54° C. $^1$H-NMR (CDCl$_3$, 300 MHz): δ 0.94 (—CH$_3$, s, 3H), 1.28 (—CH$_3$, s, 3H), 1.32 (—CH$_3$, s, 3H), 1.34~1.38 (—CH$_2$, d, 1H), 1.66 (—CH$_2$, m, 1H), 1.93 (—CH, m, 1H), 2.01 (—CH$_2$, t, 1H), 2.20 (—CH, m, 1H), 2.33 (H$_2$O, s, 2H), 2.49 (—CH$_2$, m, 1H), 4.00 (—CH, q, 1H); $^{13}$C-NMR (CDCl$_3$, 300 MHz): δ 24.11, 27.80, 28.00, 29.54, 38.21, 38.99, 40.51, 53.98, 69.26, 73.88; Elemental analysis: C$_{10}$H$_{18}$O$_2$, Calculated values C, 70.55; H, 10.66; Measured values C, 70.55; H, 10.67.

PREPARATION EXAMPLE 39

Dichloromethyl Boronic Acid Dimethyl Ester

To a 250 ml of flask was added anhydrous dichloromethane (4.26 ml, 66 mmol) and 120 ml of anhydrous tetrahydrofuran, nitrogen gas was purged, cooled down to −110° C., then a solution of n-butyl lithium in cyclohexane (25.2 ml, 60 mmol) was added dropwise slowly, stirring was continued for 1 hour at low temperature after addition was finished, then trimethyl borate (7.5 ml, 66 mmol) was added, 12 ml of 5N HCl solution was added after stirring for another 1 hour at low temperature, the resultant mixture was spontaneously warmed to room temperature. The reaction solution was transferred into a separatory funnel, the organic phase was separated out, the water layer was extracted with diethyl ether (2×10 ml), the organic phase was combined, dried over anhydrous sodium sulfate. The solvent was evaporated to give 9.3 g of white sticky solid with a yield of 99.4%. The product was directly used for the next reaction without purification.

PREPARATION EXAMPLE 40

Dichloromethyl Boronic Acid-α-pinanediol Ester

To a 25 ml of flask was added the product of α-pinanediol of Preparation example 38 (3.23 g, 0.019 mmol) and the product of dichloromethyl boronic acid dimethyl ester of Preparation example 39 (5.38 g, 0.035 mmol), then dissolved with 5 ml of THF, stirred at room temperature. The reaction was monitored by TLC and finished after 18 h. Separated by column chromatography (ethyl acetate:petroleum ether=1:20) to give 4.92 g of colorless liquid with a yield of 98.5%. $^1$H-NMR (CDCl$_3$, 300 MHz): δ 0.85 (—CH$_3$, s, 3H), 1.21 (—CH$_2$, t, 1H), 1.31 (—CH$_3$, s, 3H), 1.47 (—CH$_3$, s, 3H), 1.92~1.97 (—CH$_2$, CH, m, 2H), 2.15 (—CH, t, 1H), 2.25~2.43 (—CH$_2$, m, 2H), 4.47 (—CH, q, 1H), 5.40 (—CH, s, 1H); $^{13}$C-NMR (CDCl$_3$, 75 MHz): δ 23.92, 26.18, 26.93, 28.18, 34.98, 38.31, 39.16, 51.09, 79.41, 88.08. MS (EI): m/z 262.0 (M$^+$), Calculated value m/z 262.0.

PREPARATION EXAMPLE 41

2-methyl-4-chloro-butyl Boronic Acid-α-pinanediol Ester

The product of dichloromethyl boronic acid-α-pinanediol ester (1.18 g, 4.49 mmol) in Preparation example 40 was dissolved with 12 ml of dimethyl ether, stirred at room temperature. Nitrogen gas was purged, and cooled down to −78° C., then a solution of freshly prepared t-butyl Grignard reagent in diethyl ether (6 ml, 4.50 mmol) was added dropwise slowly. After the addition was completed, dried ZnCl$_2$ powder (0.44 g, 3.25 mmol) was added. The resultant mixture was spontaneously warmed to room temperature, continued to stir at room temperature. The reaction was monitored by TLC and finished after 18 h. MgBr$_2$ produced by the reaction and ZnCl$_2$ were removed by filtration, separated by column chromatography (ethyl acetate:petroleum ether=1:200) after being concentrated to give 1.13 g of colorless liquid with a yield of 88.5%. $^1$H-NMR (CDCl$_3$, 300 MHz): δ 0.85-0.94 (—CH$_3$, m, 9H), 1.19 (—CH, q, 1H), 1.30 (—CH$_3$, s, 3H), 1.42 (—CH$_3$, s, 3H), 1.62 (CH, m, 1H), 1.75-1.95 (—CH$_2$, m, 4H), 2.10 (—CH, t, 1H), 2.21-2.40 (—CH$_2$, m, 2H), 3.54

(—CH, m, 1H), 4.37 (—CH, q, 1H). $^{13}$C-NMR (CDCl$_3$, 75 MHz): δ 21.18, 22.84, 23.93, 25.54, 26.27, 26.97, 28.37, 35.24, 38.18, 39.27, 42.72, 51.11, 86.63; MS (EI): m/z 284.2 (M$^+$), Calculated value m/z 284.6.

PREPARATION EXAMPLE 42

2-methyl-4-amino-butyl Boronic Acid-α-pinanediol Ester Hydrochloride (LeuBdiol-NH$_2$)

To a 150 ml of eggplant type flask was added into LiN(SiMe$_3$)$_2$ (9.5 ml, 17.98 mmol), and nitrogen gas was purged, and cooled down to –78° C., then a solution of the product of 2-methyl-4-chloro-butyl boronic acid-α-pinanediol ester (4.7 g, 16.54 mmol) of Preparation example 41 in THF was added slowly using syringe, the resultant mixture was spontaneously warmed to room temperature after the addition was finished, continued stirring at room temperature. The reaction was monitored by TLC and finished after 20 h. The solvent was evaporated under reduced pressure, washed twice with diethyl ether, the residue was dissolved with 50 ml of petroleum ether, and insoluble substance was removed by filtration. The filtrate was cooled down to –78° C., 65 ml of hydrogen chloride in diethyl ether was added, then the temperature was spontaneously and slowly raised to room temperature, a large amount of milk-white solid appeared. Crystal was fully precipitated by refrigeration, filtered, and the product was washed with diethyl ether to give 2.8 g of milk-white solid with a yield of 56.2%. The product was directly used for the next reaction without purification.

EXAMPLE 1

Pinanediol N-pyrazineformyl-L-phenylalanyl-L-phenylalanyl-L-leucine Borate (5a)

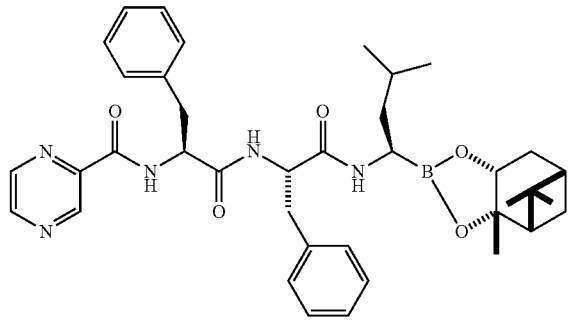

N-pyrazineformyl-L-phenylalanyl-L-phenylalanine (0.42 g, 1 mmol) of Preparation example 5 was dissolved in 7 ml of THF, HOBt (0.16 g, 1.2 mmol) and 1-ethyl-(3-dimethylaminopropyl)carbodiimide hydrochloride (0.29 g, 1.5 mmol) were added at –20° C., then reacted for 30 min followed by addition of LeuBdiol-NH$_2$ (0.3 g, 1 mmol) obtained in Preparation example 42 and N,N-diisopropylethylamine (0.26 g, 2 mmol), the mixture was stirred overnight at –20° C. TLC monitored the reaction, the after the reaction was completed, insoluble substance was removed by filtration, and solvent was evaporated under reduced pressure, the residue was dissolved with 20 ml of ethyl acetate, washed with 10% citric acid solution, 5% sodium bicarbonate solution, saturated table salt solution (3×15 ml) successively. The ethyl acetate layer was dried over anhydrous magnesium sulfate, filtered, concentrated, and the residue was separated by column chromatography to give 0.54 g of compound 4a as a white solid with a yield of 82%. m.p.: 78-80° C.; $^1$H-NMR (CDCl$_3$, 500 MHz): δ 9.31-9.26 (m, 1H), 8.82-8.77 (m, 1H), 8.58-8.54 (m, 1H), 8.23-8.19 (m, 1H), 7.32-6.99 (m, 10H), 6.48-6.42 (m, 1H), 5.72-5.67 (m, 1H), 4.80-4.77 (m, 1H), 4.59-4.55 (m, 1H), 4.36-4.33 (m, 1H), 3.19-3.09 (m, 4H), 2.90-2.88 (m, 1H), 2.36-2.22 (m, 2H), 2.08-2.03 (m, 1H), 1.94-1.86 (m, 2H), 1.47-1.39 (m, 3H), 1.30-1.28 (m, 3H), 1.29-1.21 (m, 3H), 0.90-0.83 (m, 9H); $^{13}$C-NMR (CDCl$_3$, 125 MHz): 169.86, 169.77, 163.21, 147.63, 144.33, 143.52, 142.69, 136.25, 135.94, 129.22, 129.13, 128.81, 128.45, 127.28, 126.72, 84.72, 54.73, 54.27, 51.50, 39.41, 39.37, 38.37, 38.03, 37.84, 37.64, 35.68, 28.53, 28.44, 27.05, 26.36, 26.32, 25.58, 23.96, 22.36; MS (EI): m/z 665.6 (M)$^+$.

EXAMPLE 2

N-pyrazineformyl-L-phenylalanyl-L-phenylalanyl-L-leucine Boronic Acid (6a)

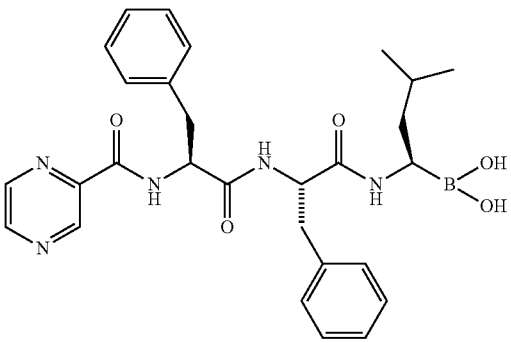 [SMILES: CC(C)C[C@H](NC(=O)[C@H](Cc1ccccc1)NC(=O)[C@H](Cc1ccccc1)NC(=O)c1cnccn1)B(O)O]

The product 5a of Example 1 (0.33 g, 0.5 mmol) was dissolved with 12 ml of acetone, to which was added NH$_4$OAC solution (0.1N, 11.6 ml) followed by NaIO$_4$ (0.32 g, 1.5 mmol), then reacted under stirring at room temperature. TLC indicated the reaction was completed after 10 h. To the reaction solution, sodium hydroxide solution (2N, 0.5 ml) was added, and the resultant solution was extracted with dichloromethane. The pH value of the solution was adjusted to about 3 using concentrated hydrochloric acid. Then extracted with dichloromethane (3×15 ml), the organic phase was combined, dried over anhydrous sodium sulfate followed by filtration, then the solvent was evaporated to give 0.19 g of light yellow solid 5a with a yield of 72.1%. m.p.: 112-114° C. $^1$H-NMR (CDCl$_3$, 300 MHz): δ 0.88 (—CH$_3$, d, 3H), 0.90 (—CH$_3$, d, 3H), 1.25~2.17 (—CH$_2$, —CH, —B(OH)$_2$, m, 5H), 2.96~3.17 (—CH, m, 5H), 4.65~4.77 (—CH, m, 2H), 6.38~6.42 (—CONH, m, 1H), 6.84~7.07 (-Ph, —CONH, m, 6H), 7.24~7.29 (-Ph, m, 5H), 8.18 (—CONH, s, 1H), 8.53 (-Pyz, s, 1H), 8.77 (-Pyz, s, 1H), 9.15~9.26 (-Pyz, m, 1H); $^{13}$C-NMR (CDCl$_3$, 75 MHz): δ 22.51, 23.17, 25.66, 37.30, 37.54, 51.70, 53.64, 54.96, 126.75, 127.41, 128.41, 128.54, 128.88, 129.20, 135.66, 135.89, 142.72, 143.32, 144.28, 147.75, 163.32, 163.58, 169.74, 170.01; MS (ESI): m/z 530.4907 (M–H); FT-MS: m/z 532.27179 (M+H), Calculated value 532.27258.

EXAMPLE 3

Pinanediol N-pyrazineformyl-L-naphthylalanyl-L-phenylalanyl-L-leucine Borate (5b)

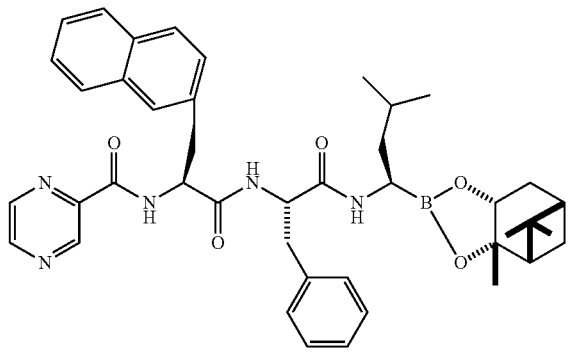

Using the product of Preparation example 8 as a raw material, the synthesis and work-up were analogous to that described in Example 1, and a white solid was obtained with a yield of 87%, m.p.: 98-100° C. $^1$H-NMR (CDCl$_3$, 300 MHz): δ 9.13 (s, 1H), 8.74 (d, J=2.4 Hz, 1H), 8.48 (d, J=2.1 Hz, 1H), 8.23-8.20 (d, J=7.5 Hz, 1H), 7.80-7.69 (m, 4H), 7.46-7.43 (m, 2H), 7.35 (d, J=8.4 Hz, 1H), 7.02-6.95 (m, 5H), 6.53-6.45 (m, 1H), 4.65-4.57 (m, 1H), 4.29-4.27 (m, 1H), 3.40-3.26 (m, 2H), 3.13-3.02 (m, 1H), 2.95-2.84 (m, 1H), 2.35-2.27 (m, 1H), 2.20-2.15 (m, 1H), 2.04-1.99 (m, 1H), 1.89-1.80 (m, 1H), 1.39-1.23 (m, 12H), 0.87-0.83 (m, 9H); $^{13}$C-NMR (CDCl$_3$, 75 MHz): 170.39, 169.85, 163.19, 147.57, 144.32, 143.59, 142.71, 136.13, 133.51, 133.46, 132.47, 129.22, 128.56, 128.35, 128.01, 127.66, 127.57, 127.51, 126.65, 126.24, 125.84, 54.55, 54.42, 53.64, 51.35, 39.70, 39.55, 38.19, 37.85, 37.74, 35.50, 28.61, 27.08, 26.24, 25.36, 25.21, 24.03, 22.97, 22.01; HRMS Calculated value C$_{42}$H$_{51}$BN$_5$O$_5$ (M+1)$^+$ 716.3978, Measured value 716.3986.

EXAMPLE 4

N-pyrazineformyl-L-naphthylalanyl-L-phenylalanyl-L-leucine Boronic Acid (6b)

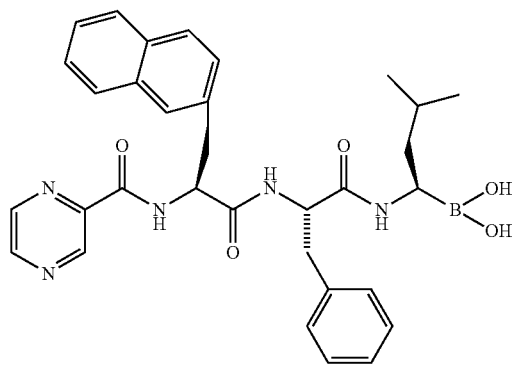 [SMILES: CC(C)C[C@H](NC(=O)[C@H](Cc1ccccc1)NC(=O)[C@H](Cc1ccc2ccccc2c1)NC(=O)c1cnccn1)B(O)O]

In a 100 ml of rounded bottom flask, the product of boronic ester 5b of Example 3 (0.357 g, 0.5 mmol) was dissolved in anhydrous dichloromethane, a solution of boron tribromide (1N, 2.5 ml) in dichloromethane was added dropwise, stirred under the condition of ice bath for 2 hours, then the reaction was monitored by TLC. After the reaction was completed, 50 ml of water was added dropwise to quench the reaction, extracted with dichloromethane (15 ml×4), the organic phase was combined, washed with saturated table salt solution (15 ml×4), dried over anhydrous sodium sulfate, then filtered and concentrated, 0.18 g of milk-white solid was obtained by re-crystallization from ether/dichloromethane. The yield was 63.5%. m.p.: 134-135° C. $^1$H-NMR (CDCl$_3$, 300 MHz): δ 9.15 (s, 1H), 8.73 (d, J=2.4 Hz, 1H), 8.46 (d, J=2.1 Hz, 1H), 8.24-8.17 (m, 1H), 7.76-7.66 (m, 4H), 7.44-7.40 (m, 3H), 7.32-7.25 (m, 1H), 6.90-6.86 (m, 5H), 6.52-6.46 (m, 2H), 4.81-4.67 (m, 2H), 3.31-3.26 (m, 1H), 3.11 (d, J=6.9 Hz, 2H), 2.93-2.89 (m, 1H), 1.92 (s, br, 2H), 1.55-1.21 (m, 3H), 0.85-0.82 (m, 6H); $^{13}$C-NMR (CDCl$_3$, 75 MHz): 172.96, 169.99, 163.61, 147.70, 144.24, 143.30, 142.70, 137.28, 135.61, 133.47, 133.19, 132.49, 129.13, 128.64, 128.35, 128.07, 127.64, 127.55, 127.11, 126.71, 126.39, 125.92, 54.88, 51.86, 39.85, 39.34, 37.43, 37.23, 36.88, 25.68, 23.12, 22.46. HRMS Calculated value C$_{32}$H$_{36}$BN$_5$O$_5$ (M−1)$^-$ 580.2727, Measured value 580.2736.

EXAMPLE 5

Pinanediol N-pyrazineformyl-L-phenylalanyl-L-tyrosyl-L-leucine Borate (5c)

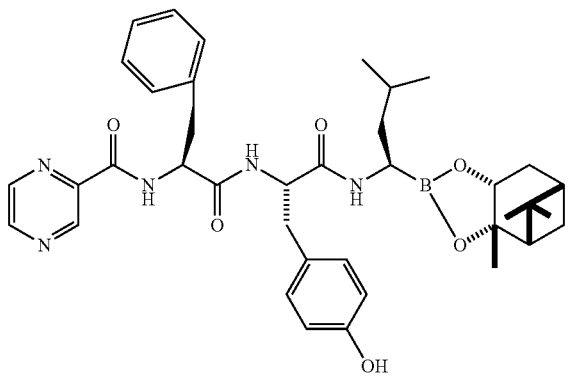

Using the product of Preparation example 10 as a raw material, the synthesis and work-up were analogous to that described in Example 1, a light yellow solid was obtained with a yield of 81%. m.p.: 119-120° C. $^1$H-NMR (CD$_3$OD, 300 MHz): δ 9.18 (s, 1H), 8.68 (d, J=10.2 Hz, 1H), 8.48 (s, 1H), 8.26 (d, J=7.5 Hz, 1H), 7.82-7.74 (m, 1H), 7.27-7.18 (m, 5H), 6.80-6.76 (m, 3H), 6.49-6.40 (m, 2H), 4.82-4.61 (m, 2H), 4.29-4.27 (d, J=8.1 Hz, 1H), 3.13-3.06 (m, 2H), 2.95-2.84 (m, 3H), 2.35-2.27 (m, 2H), 2.04-2.02 (m, 1H), 1.85-1.80 (m, 2H), 1.43-1.26 (m, 9H), 0.88-0.83 (m, 9H); $^{13}$C-NMR (CD$_3$OD, 75 MHz): 170.17, 163.36, 155.62, 147.61, 143.96, 143.44, 142.83, 135.95, 130.37, 129.21, 128.78, 127.47, 127.23, 126.61, 126.44, 115.34, 85.30, 54.86, 54.74, 52.91, 51.54, 40.16, 39.82, 39.64, 38.10, 37.57, 36.97, 35.80, 35.69, 28.73, 27.10, 26.28, 25.41, 24.04, 23.06, 22.97, 22.03, 21.95; HRMS Calculated value C$_{38}$H$_{46}$BN$_5$O$_6$ (M+1)$^+$ 682.3770, Measured value 682.3767.

EXAMPLE 6

N-pyrazineformyl-L-phenylalanyl-L-tyrosyl-L-leucine Boronic Acid (6c)

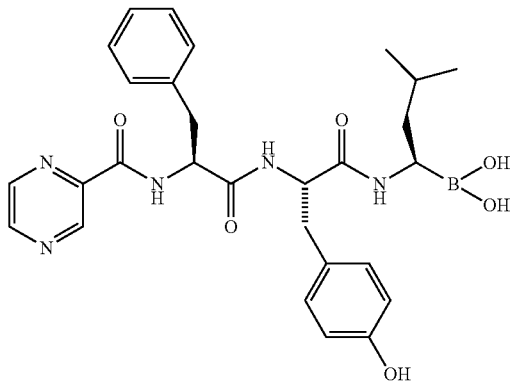 [SMILES: CC(C)C[C@H](NC(=O)[C@H](Cc1ccc(O)cc1)NC(=O)[C@H](Cc1ccccc1)NC(=O)c1cnccn1)B(O)O]

Using the product 5c of Example 5 as a raw material, the synthesis and work-up were analogous to that described in Example 4, a yellow solid was obtained with a yield of 56.3%. m.p.: 298-300° C. $^1$H-NMR (CD$_3$OD, 300 MHz): δ 9.13 (s, 1H), 8.78 (t, J=2.4 Hz, 1H), 8.67-8.66 (dd, J=1.2, 2.4 Hz, 1H), 7.23-7.16 (m, 5H), 7.16-7.01 (m, 2H), 6.66-6.18 (m, 2H), 4.80-4.73 (m, 2H), 3.20-3.18 (m, 1H), 3.08-3.02 (m, 3H), 2.68-2.56 (m, 1H), 1.62-1.54 (m, 2H), 1.33-1.26 (m, 2H), 1.14-1.04 (m, 2H), 0.89-0.83 (m, 6H); $^{13}$C-NMR (CD$_3$OD, 300 MHz): 177.69, 173.05, 165.13, 164.95, 157.77, 157.68, 148.79, 145.59, 144.96, 144.79, 144.49, 137.82, 131.47, 131.35, 130.34, 129.56, 127.97, 127.40, 127.16, 116.41, 56.11, 55.90, 52.87, 52.67, 40.70, 38.82, 38.49, 37.65, 37.30, 26.83, 26.61, 23.89, 23.69, 22.31, 21.83. HRMS Calculated value C$_{28}$H$_{34}$BN$_5$O$_6$ (M−1)$^-$ 546.2529, Measured value 546.2527.

EXAMPLE 7

Pinanediol N-pyrazineformyl-L-tyrosyl-L-phenylalanyl-L-leucine Borate (5d)

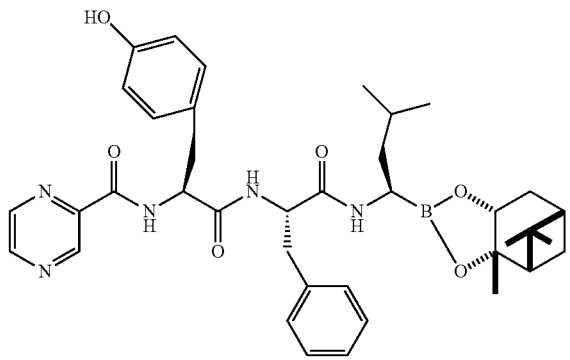

Using the product of Preparation example 13 as a raw material, preparation was carried out according to the synthetic approach of Example 1, and a light yellow solid was obtained with a yield of 80%. m.p.: 90-92° C. $^1$H-NMR (CD$_3$OD, 300 MHz): δ 9.29 (s, 1H), 8.74 (d, J=2.4 Hz, 1H), 8.50 (d, J=2.1 Hz, 1H), 8.26 (d, J=7.8 Hz, 1H), 7.11-6.99 (m, 8H), 6.74 (d, J=8.4 Hz, 2H), 6.74-6.71 (m, 1H), 6.50-6.42 (m, 1H), 4.70-4.26 (m, 1H), 4.51-4.27 (m, 1H), 4.29-4.17 (m, 2H), 3.07-2.93 (m, 5H), 2.37-2.31 (m, 1H), 2.21-2.16 (m, 1H), 2.06-2.03 (m, 1H), 1.90-1.80 (m, 2H), 1.40-1.26 (m, 6H), 0.90-0.79 (m, 12H); $^{13}$C-NMR (CD$_3$OD, 75 MHz): 171.36, 170.18, 163.03, 155.47, 147.50, 144.29, 143.74, 142.73, 135.95, 130.29, 130.15, 129.31, 128.50, 127.51, 126.83, 116.47, 116.64, 85.33, 55.08, 53.19, 51.55, 39.73, 39.64, 39.40, 38.23, 38.16, 37.44, 37.14, 35.67, 28.73, 28.54, 27.14, 26.30, 25.44, 24.07, 22.98, 22.02; HRMS Calculated value C$_{38}$H$_{49}$BN$_5$O$_6$ (M+1)$^+$ 682.3770, Measured value 682.3795.

EXAMPLE 8

N-pyrazineformyl-L-tyrosyl-L-phenylalanyl-L-leucine Boronic Acid (6d)

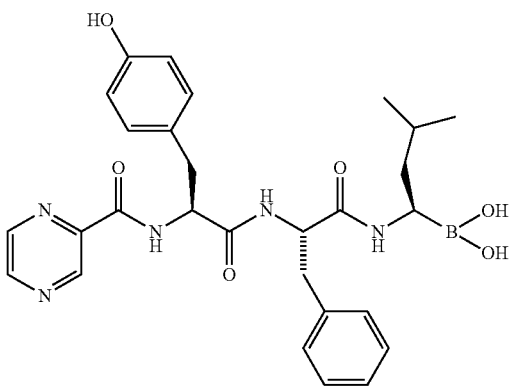 [SMILES: CC(C)C[C@H](NC(=O)[C@H](Cc1ccccc1)NC(=O)[C@H](Cc1ccc(O)cc1)NC(=O)c1cnccn1)B(O)O]

Using the product 5d of Example 7 as a raw material, the synthesis and work-up method were analogous to that described in Example 4, and a yellow solid was obtained with a yield of 71.5%. m.p.: 219-221° C. $^1$H-NMR (CD$_3$OD, 300 MHz): δ 9.15 (s, 1H), 8.78 (d, J=2.4 Hz, 1H), 8.66 (d, J=2.1 Hz, 1H), 7.24-7.19 (m, 5H), 7.13-7.00 (m, 2H), 6.97-6.62 (m, 2H), 4.80-4.71 (m, 2H), 3.11-3.06 (m, 3H), 2.93-2.87 (m, 1H), 2.64-2.54 (m, 1H), 1.62-1.54 (m, 2H), 1.40-1.29 (m, 2H), 1.16-1.11 (m, 2H), 0.92-0.81 (m, 6H); $^{13}$C-NMR (CD$_3$OD, 75 MHz): 177.20, 173.18, 164.92, 157.51, 148.68, 145.62, 144.93, 144.73, 137.17, 136.96, 131.36, 130.46, 130.33, 129.69, 129.62, 128.25, 128.19, 116.32, 56.34, 56.17, 52.61, 40.77, 38.46, 38.11, 37.82, 26.62, 23.86, 21.91. ESI: MS (ESI) Measured value: (M+Na/z)$^+$ 570.2168, Calculated value 570.2500 (M+Na).

EXAMPLE 9

Pinanediol N-pyrazineformyl-L-leucyl-L-phenylalanyl-L-leucine Borate (5e)

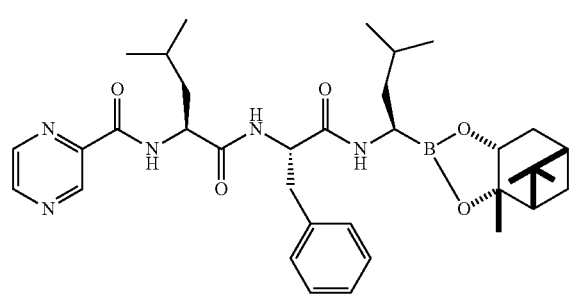

Using the product of preparation Example 18 as a raw material, the preparation was carried out according to the synthetic approach of Example 1 with a yield of 87%. A white solid was obtained, m.p.: 63-65° C. $^1$H-NMR (CDCl$_3$, 500 MHz): δ 9.32 (s, 1H), 8.78-8.67 (m, 1H), 8.55-8.21 (m, 1H), 8.10-7.95 (m, 1H), 7.15-6.99 (m, 6H), 6.04-5.96 (m, 1H), 4.65-4.34 (m, 2H), 4.30-4.15 (m, 1H), 3.22-3.01 (m, 2H), 2.37-2.22 (m, 2H), 2.12-2.04 (m, 1H), 1.93-1.90 (m, 2H), 1.76-1.63 (m, 3H), 1.48-1.39 (m, 1H), 1.28 (s, 3H), 1.29-1.22 (m, 3H), 0.94-0.90 (m, 6H), 0.86-0.83 (m, 9H); $^{13}$C-NMR (CDCl$_3$, 125 MHz): 171.35, 170.30, 163.15, 147.47, 144.38, 143.72, 142.63, 136.451, 129.10, 128.37, 126.66, 84.55, 54.50, 52.02, 51.45, 40.73, 38.31, 38.03, 37.95, 37.77, 35.63, 28.48, 27.00, 26.26, 25.52, 24.78, 23.91, 22.89, 22.29, 21.78; MS (EI): m/z 631.6 (M)$^+$.

EXAMPLE 10

N-pyrazineformyl-L-leucyl-L-phenylalanyl-L-leucine Boronic Acid (6e)

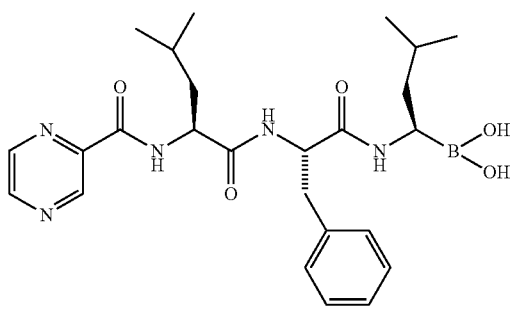 [SMILES: CC(C)C[C@H](NC(=O)[C@H](Cc1ccccc1)NC(=O)[C@H](CC(C)C)NC(=O)c1cnccn1)B(O)O]

Using the product 5e of Example 9 as a raw material, the synthetic approach and work-up were analogous to that described in Example 2. The solvent was evaporated to give 19.7 mg of yellow solid with a yield of 68.4%. m.p.: 113-116° C. $^1$H-NMR (CDCl$_3$, 300 MHz): δ 0.78~0.82 (—CH$_3$, m, 13H), 1.19~1.57 (—CH$_2$, —CH, —B (OH)$_2$, m, 7H), 1.95 (—CH, d, 1H), 2.89~3.09 (—CH, —CH$_2$, m, 3H), 4.28~4.41 (—CH, m, 1H), 4.61~4.76 (—CH, m, 1H), 6.92~7.02 (-Ph, —CONH, m, 6H), 7.19~7.25 (—CONH, m, 1H), 7.96~8.02 (—CONH, m, 1H), 8.47 (-Pyz, s, 1H), 8.72 (-Pyz, s, 1H), 9.16~9.25 (-Pyz, m, 1H); MS (ESI) Measured value m/z 496.3710 (M–H), Calculated value 497.2809.

EXAMPLE 11

Pinanediol N-pyrazineformyl-L-leucyl-L-naphthylalanyl-L-leucineborate (5f)

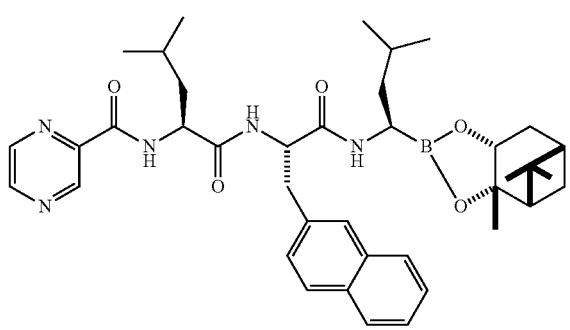

Using the product of Preparation example 20 as a raw material, the synthesis and work-up method were analogous to that described in Example 1, and a white solid was obtained with a yield of 85%, m.p.: 140-142° C. $^1$H-NMR (CDCl$_3$, 300 MHz): δ 9.195 (d, J=1.5 Hz, 1H), 8.71 (d, J=2.4 Hz, 1H), 8.40 (t, J=1.2 Hz, 1H), 7.93 (d, J=8.1 Hz, 1H), 7.66-7.61 (m, 4H), 7.36-7.32 (m, 3H), 6.75 (d, J=7.8 Hz, 1H), 6.00 (d, J=4.8 Hz, 1H), 4.78-4.71 (m, 1H), 4.59-4.53 (m, 1H), 4.27 (dd, J=8.7 Hz, 1H), 3.23 (d, J=6.6 Hz, 2H), 3.14-3.10 (m, 1H), 2.28-2.20 (m, 1H), 2.17-2.08 (m, 1H), 2.00-2.05 (m, 1H), 1.87-1.57 (m, 6H), 1.41-1.27 (m, 9H), 0.92-0.90 (m, 6H), 0.83-0.77 (m, 9H); $^{13}$C-NMR (CDCl$_3$, 75 MHz): 171.05, 170.61, 163.13, 147.52, 144.24, 143.45, 142.59, 142.47, 133.933, 133.25, 132.22, 128.13, 127.99, 127.48, 127.26, 125.95, 125.52, 85.83, 53.06, 51.98, 51.88, 51.32, 40.63, 39.68, 39.56, 38.19, 35.48, 28.56, 27.10, 26.23, 25.33, 25.22, 24.78, 24.04, 22.89, 21.80; HRMS Calculated value C$_{39}$H$_{53}$BN$_5$O$_5$ (M+1)$^+$ 682.4134, Measured value 682.4155.

EXAMPLE 12

N-pyrazineformyl-L-leucyl-L-naphthylalanyl-L-leucine Boronic Acid (6f)

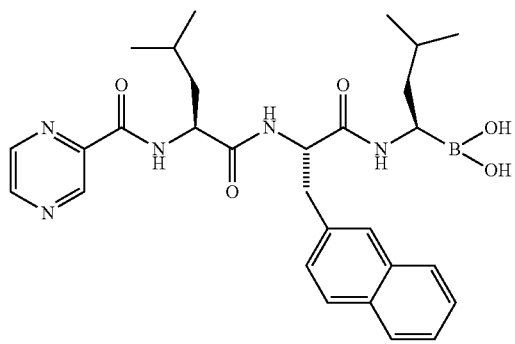 [SMILES: CC(C)C[C@H](NC(=O)[C@H](Cc1ccc2ccccc2c1)NC(=O)[C@H](CC(C)C)NC(=O)c1cnccn1)B(O)O]

Using the product 5f of Example 11 as a raw material, the synthesis and work-up method were analogous to that described in Example 4, and a milk-white solid was obtained with a yield of 56.3%, m.p.: 157-159° C. $^1$H-NMR (CDCl$_3$, 300 MHz): δ 9.13-9.10 (m, 1H), 8.67 (s, 1H), 8.36 (s, 1H), 7.98-7.94 (m, 2H), 7.59-7.29 (m, 7H), 7.22-7.19 (m, 2H), 4.98-4.84 (m, 1H), 4.41-4.37 (m, 1H), 3.46-3.35 (m, 2H), 3.24-3.10 (m, 1H), 1.71-1.25 (m, 8H), 0.88-0.78 (m, 12H); $^{13}$C-NMR (CDCl$_3$, 75 MHz): 171.48, 163.92, 147.65, 144.15, 143.31, 143.07, 142.56, 133.56, 133.22, 132.25, 129.16, 128.69, 128.24, 127.51, 127.10, 125.98, 125.58, 52.95, 52.77, 51.91, 41.12, 40.23, 36.76, 25.68, 24.72, 23.12, 22.83, 22.44, 21.69. HRMS Calculated value C$_{29}$H$_{37}$BN$_5$O$_5$ (M–1)$^-$ 546.2893, Measured value 546.2906.

EXAMPLE 13

Pinanediol N-pyrazineformyl-L-phenylalanyl-L-naphthylalanyl-L-leucine Borate (5g)

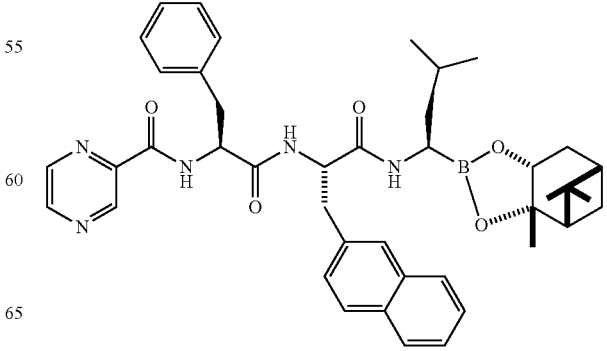

Using the product of Preparation example 22 as a raw material, the synthesis and work-up method were analogous to that described in Example 1, and a white solid was obtained, and the yield was 86%, m.p.: 97-98° C. $^1$H-NMR (CDCl$_3$, 300 MHz): δ 9.13-9.09 (m, 1H), 8.66 (d, J=2.4 Hz, 1H), 8.34 (d, J=1.2 Hz, 1H), 8.10 (d, J=7.5 Hz, 1H), 7.62-7.46 (m, 3H), 7.41-7.21 (m, 9H), 6.53-6.45 (m, 1H), 5.99-5.78 (m, 1H), 4.76-4.72 (m, 1H), 4.25 (dd, J=8.7 Hz, 1H), 3.29-3.22 (m, 1H), 3.16-3.14 (d, J=6.3 Hz, 2H), 3.11-3.04 (m, 1H), 2.29-2.26 (m, 1H), 2.17-2.12 (m, 1H), 2.02-1.98 (m, 1H), 1.86-1.67 (m, 2H), 1.38-1.25 (m, 12H), 0.87-0.81 (m, 9H); $^{13}$C-NMR (CDCl$_3$, 75 MHz): 170.53, 169.85, 163.19, 147.50, 144.04, 143.28, 143.15, 142.63, 135.96, 135.89, 133.66, 133.54, 133.20, 132.19, 129.20, 128.78, 128.14, 127.96, 127.48, 127.28, 127.21, 125.92, 125.53, 54.56, 53.36, 53.01, 51.34, 39.88, 39.70, 39.57, 38.05, 37.60, 35.57, 28.57, 27.09, 26.22, 25.32, 25.16, 24.03, 22.91, 22.01, 21.92; HRMS Calculated value C$_{42}$H$_{51}$BN$_5$O$_5$ (M+1)$^+$ 716.3978, Measured value 716.3996.

EXAMPLE 14

N-pyrazineformyl-L-phenylalanyl-L-naphthylalanyl-L-leucine Boronic Acid (6g)

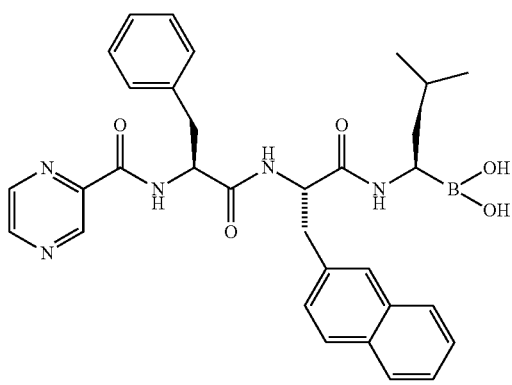 [SMILES: CC(C)C[C@H](NC(=O)[C@H](Cc1ccc2ccccc2c1)NC(=O)[C@H](Cc1ccccc1)NC(=O)c1cnccn1)B(O)O]

Using the product 5g of Example 13 as a raw material, the synthetic approach and work-up were analogous to that described in Example 4, and a milk-white solid was obtained with a yield of 53%, m.p.: 137-138° C. $^1$H-NMR (CDCl$_3$, 300 MHz): δ 9.90 (s, 1H), 8.61 (s, 1H), 8.26 (s, 1H), 8.09-7.98 (m, 1H), 7.50-7.23 (m, 12H), 7.19-7.07 (m, 1H), 6.73-6.56 (m, 2H), 4.88-4.76 (m, 1H), 4.72-4.67 (m, 1H), 3.33-3.28 (m, 1H), 3.14-3.12 (d, J=6.3 Hz, 2H), 3.02-2.97 (m, 1H), 2.04 (s, br, 2H), 1.51-1.42 (m, 3H), 0.87-0.80 (m, 6H); $^{13}$C-NMR (CDCl$_3$, 75 MHz): 173.10, 170.06, 163.51, 147.59, 143.90, 142.95, 142.86, 142.64, 142.52, 135.90, 135.70, 133.45, 133.23, 133.07, 132.14, 129.29, 128.88, 128.24, 127.94, 127.46, 127.14, 125.90, 125.53, 54.94, 51.96, 42.92, 39.98, 37.26, 36.92, 25.69, 23.14, 22.56; HRMS Calculated value C$_{32}$H$_{35}$BN$_5$O$_5$ (M−1)$^-$ 580.2736, Measured value 580.2729.

EXAMPLE 15

Pinanediol N-pyrazineformyl-L-naphthylalanyl-L-naphthylalanyl-L-leucine Borate (5h)

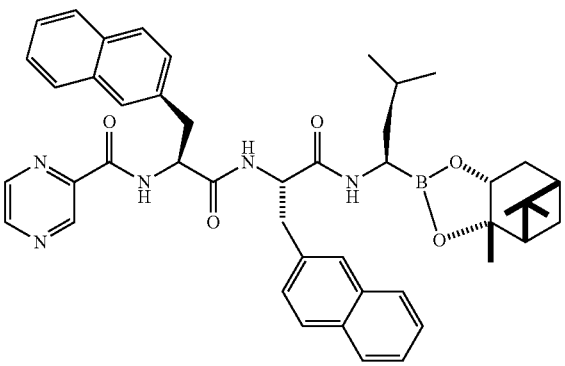

Using the product of Preparation example 24 as a raw material, the synthesis and work-up was analogous to that described in Example 1, and a white solid was obtained with a yield of 82%, m.p.: 136-137° C. $^1$H-NMR (CD$_3$OD, 300 MHz): δ 9.10 (s, 1H), 8.63 (d, J=2.4 Hz, 1H), 8.26 (d, J=2.4 Hz, 1H), 8.12-8.02 (m, 1H), 7.81-7.57 (m, 6H), 7.53-7.32 (m, 8H), 7.20-7.17 (dd, J=1.8, 8.4 Hz, 2H), 6.51-6.49 (m, 1H), 6.00 (d, J=5.1 Hz, 1H), 4.87-4.72 (m, 2H), 4.28-4.24 (dd, J=1.5, 8.7 Hz, 1H), 3.33-3.31 (d, J=6.3 Hz, 2H), 3.24-3.22 (m, 1H), 3.07-3.00 (m, 1H), 2.33-2.25 (m, 1H), 2.18-2.13 (m, 1H), 2.04-2.00 (m, 1H), 1.87-1.67 (m, 2H), 1.36-1.25 (m, 8H), 0.87-0.74 (m, 12H); $^{13}$C-NMR (CD$_3$OD, 75 MHz): 170.46, 169.85, 163.22, 147.46, 144.00, 143.16, 142.61, 142.49, 133.58, 133.45, 133.34, 132.50, 132.13, 128.58, 127.97, 127.71, 127.57, 127.44, 126.31, 125.90, 125.52, 85.76, 54.41, 53.30, 51.35, 39.58, 38.19, 37.98, 37.59, 35.50, 28.59, 27.10, 26.24, 25.33, 25.18, 24.04, 21.96; HRMS Calculated value C$_{46}$H$_{53}$N$_5$O$_5$ (M+1)$^+$ 766.4134, Measured value 766.4148.

EXAMPLE 16

N-pyrazineformyl-L-naphthylalanyl-L-naphthylalanyl-L-leucine Boronic Acid (6h)

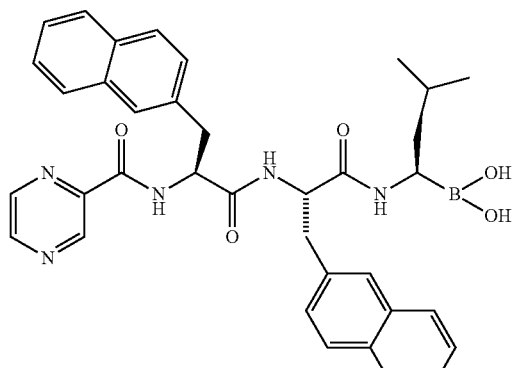

Using the product 5h of Example 15 as a raw material, the synthetic approach and work-up was analogous to that described in Example 4, and a milk-white solid was obtained with a yield of 72.1%, m.p.: 145-146° C. $^1$H-NMR (CDCl$_3$, 300 MHz): δ 8.95 (s, 1H), 8.54 (s, 1H), 8.16 (s, 1H), 8.17-8.11 (m, 1H), 7.74-7.16 (m, 14H), 7.08-6.95 (m, 2H), 6.87-6.50 (m, 2H), 4.95-4.87 (m, 1H), 4.79-4.68 (m, 1H), 3.28-3.26 (m, 2H), 3.00-2.86 (m, 1H), 2.33 (s, br, 2H), 1.38-1.35 (m, 3H), 0.81-0.79 (m, 6H); $^{13}$C-NMR (CDCl$_3$, 75 MHz): 170.18, 169.61, 163.56, 147.51, 143.79, 141.90, 142.55, 133.42, 133.126, 133.01, 132.46, 132.07, 128.58, 128.09, 127.39, 127.14, 127.01, 126.32, 125.94, 125.83, 125.49, 54.79, 51.52, 39.78, 37.49, 37.30, 36.95, 25.64, 23.09, 22.39, 22.19; HRMS Calculated value C$_{36}$H$_{37}$BN$_5$O$_5$ (M−1)$^-$ 630.2893, Measured value 630.2895.

EXAMPLE 17

Pinanediol N-pyrazineformyl-L-tryptophyl-L-phenylalanyl-L-leucine Borate (5i)

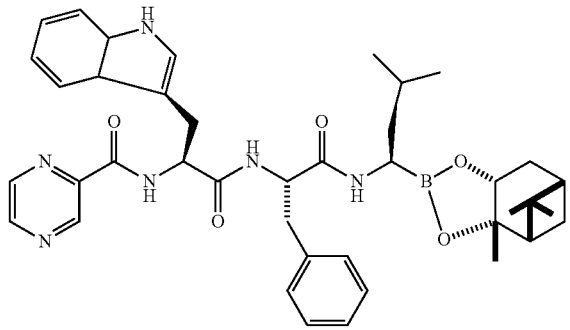

Using the product of Preparation example 26 as a raw material, the synthesis and work-up were analogous to that described in Example 1, and a white solid was obtained with a yield of 78%, m.p.: 127-129° C. $^1$H-NMR (CDCl$_3$, 300 MHz): δ 9.24 (s, 1H), 8.76 (d, J=2.4 Hz, 1H), 8.51 (d, J=2.4 Hz, 1H), 8.50-8.46 (m, 1H), 8.22-8.14 (m, 1H), 7.40-7.38 (m, 5H), 7.01-6.88 (m, 4H), 6.78-6.58 (m, 1H), 6.09-5.97 (m, 1H), 5.75-5.71 (m, 2H), 4.82-4.75 (m, 2H), 3.51-3.45 (m, 1H), 3.31-3.01 (m, 4H), 1.25-1.23 (m, 10H), 0.99-0.89 (m, 8H), 0.88-0.85 (m, 6H); MS (EI) m/z 703.6 (M−1)$^-$.

EXAMPLE 18

N-pyrazineformyl-L-tryptophyl-L-phenylalanyl-L-leucine Boronic Acid (6i)

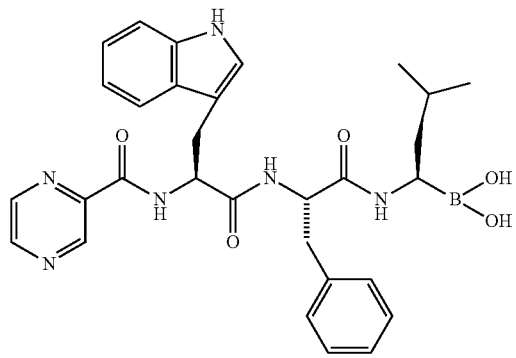 [SMILES: CC(C)C[C@H](NC(=O)[C@H](Cc1ccccc1)NC(=O)[C@H](Cc1c[nH]c2ccccc12)NC(=O)c1cnccn1)B(O)O]

Using the product 5i of Example 17 as a raw material, the synthesis and work-up were analogous to that described in Example 2, and the solvent was evaporated to give 11.4 mg of yellow sticky solid with a yield of 49.2%. $^1$H-NMR (CDCl$_3$, 300 MHz): δ 0.79 (—CH$_3$, d, 6H), 1.40~1.60 (—CH$_2$, —CH, m, 3H), 1.97~2.13 (—CH$_2$, —B (OH)$_2$, m, 10H), 3.15~3.19 (—CH, m, 1H), 3.53~3.58 (—CH, m, 1H), 3.75~3.98 (—CH, m, 1H), 4.87~4.98 (—CH, m, 1H), 5.05 (—CH, s, 1H), 6.89 (—CONH, m, 1H), 7.16~7.19 (-Ph, indole, m, 9H), 8.06 (—CONH, d, 1H), 8.64 (-Pyz, d, 1H), 9.17 (-Pyz, s, 1H), 9.28 (-Pyz, d, 1H), 9.72 (—NH, s, 1H).

EXAMPLE 19

Pinanediol N-pyrazineformyl-L-phenylalanyl-L-tyrosyl-L-leucine Borate (5j)

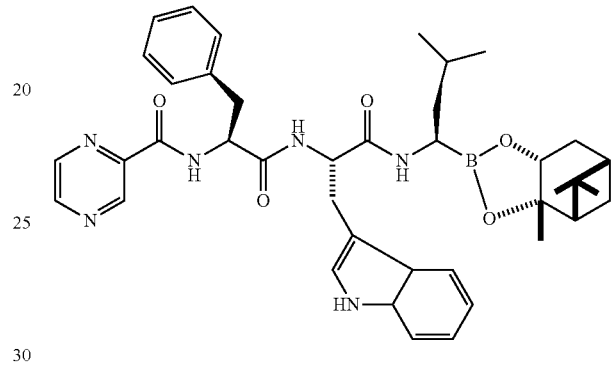

Using the product of Preparation example 30 as a raw material, the synthesis and work-up were analogous to that described in Example 1, and a light yellow solid was obtained with a yield of 79%, m.p.: 153-155° C. $^1$H-NMR (CDCl$_3$, 300 MHz): δ 9.08 (s, 1H), 8.73-8.69 (m, 1H), 8.48 (s, 1H), 8.34 (s, 1H), 8.11-7.94 (m, 1H), 7.32-7.21 (m, 5H), 7.08-6.88 (m, 4H), 6.62-6.42 (m, 1H), 6.01 (s, 1H), 5.65-5.58 (m, 2H), 4.38-4.29 (m, 2H), 3.20-3.01 (m, 4H), 1.40-1.24 (m, 10H), 0.99-0.89 (m, 8H), 0.83-0.80 (m, 6H); MS (EI) m/z 704.7 (M$^+$).

EXAMPLE 20

N-pyrazineformyl-L-phenylalanyl-L-tryptophyl-L-leucine Boronic Acid (6j)

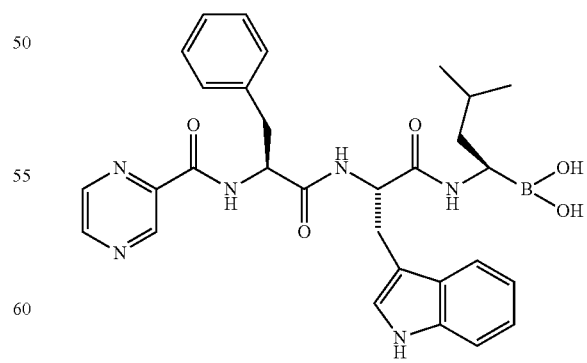

Using the product 5j of Example 19 as a raw material, the synthetic approach and work-up was analogous to that described in Example 2, and the solvent was evaporated to give 49.3 mg of yellow sticky solid with a yield of 42.4%.

¹H-NMR (CDCl₃, 300 MHz): δ 0.81 (—CH₃, m, 6H), 1.23~1.45 (—CH₂, —CH, m, 3H), 1.89~2.07 (—CH₂, —B(OH)₂, m, 10H), 3.05~3.11 (—CH, m, 1H), 3.33~3.48 (—CH, m, 1H), 3.45~3.78 (—CH, m, 1H), 4.64~4.81 (—CH, m, 1H), 5.25 (—CH, d, 1H), 6.76 (—CONH, m, 1H), 7.08~7.16 (-Ph, indole, m, 9H), 8.12 (—CONH, d, 1H), 8.57 (-Pyz, d, 1H), 9.07 (-Pyz, d, 1H), 9.21 (-Pyz, d, 1H), 9.28 (—NH, d, 1H).

EXAMPLE 21

Pinanediol N-pyrazineformyl-L-phenylalanyl-L-leucyl-L-leucine Borate (5k)

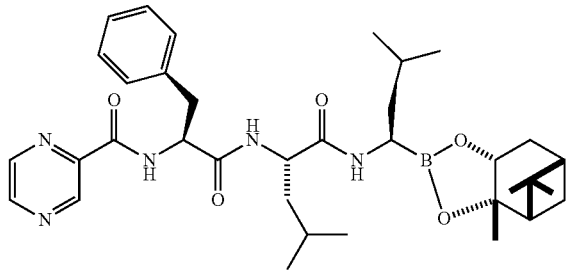

Using the product of preparation Example 32 as a raw material, the synthesis and work-up were analogous to that described in Example 1, and a white solid was obtained with a yield of 81%. m.p.: 68-70° C. ¹H-NMR (CDCl₃, 300 MHz): δ 9.33 (s, 1H), 8.76-8.73 (d, 1H), 8.54 (s, 1H), 8.29-8.10 (m, 1H), 7.29-7.25 (m, 5H), 6.39-6.31 (m, 2H), 4.82-4.79 (m, 1H), 4.44-4.41 (m, 1H), 4.30-4.27 (m, 1H), 3.22-3.19 (m, 3H), 2.32-2.17 (m, 3H), 2.05-2.02 (m, 1H), 1.89-1.27 (m, 14H), 0.96-0.83 (m, 15H); MS (EI) m/z 631.6 (M⁺).

EXAMPLE 22

N-pyrazineformyl-L-phenylalanyl-L-leucyl-L-leucine Boronic Acid (6k)

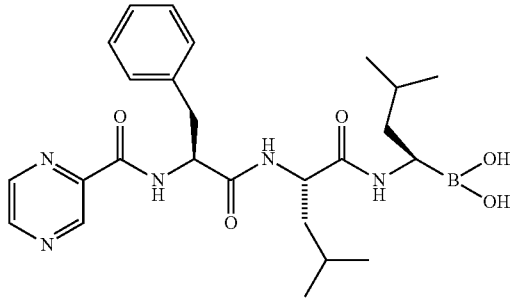 [SMILES: CC(C)C[C@H](NC(=O)[C@H](CC(C)C)NC(=O)[C@H](Cc1ccccc1)NC(=O)c1cnccn1)B(O)O]

Using the product 5k of Example 21 as a raw material, the synthetic approach and work-up was analogous to that described in Example 2, and the solvent was evaporated to give 16.7 mg of yellow solid with a yield of 73.2%, m.p.: 116-118° C. ¹H-NMR (CDCl₃, 300 MHz): δ 9.30-9.21 (m, 1H), 8.74 (s, 1H), 8.47 (s, 1H), 8.33-8.29 (m, 1H), 7.32-7.22 (m, 6H), 6.99-6.91 (m, 1H), 4.93-4.57 (m, 2H), 3.21 (s, 2H), 2.85-2.58 (m, 1H), 2.18-1.25 (m, 8H), 0.96-0.82 (m, 12H); MS (ESI) Measured value: m/z 496.3977 (M–H), Calculated value: 497.2809.

EXAMPLE 23

Pinanediol N-pyrazineformyl-L-leucyl-L-leucyl-L-leucine Borate (5l)

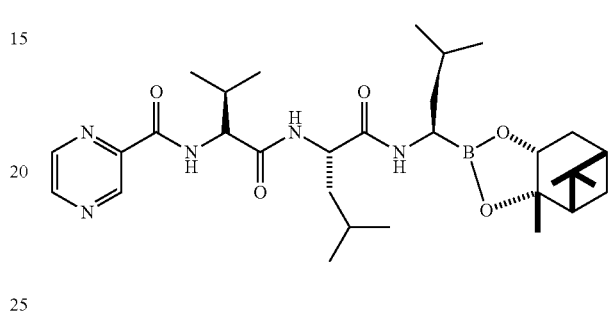

Using the product of Preparation example 34 as a raw material, the synthetic approach and work-up was analogous to that described in Example 1, and a sticky solid was obtained with a yield of 87%. ¹H-NMR (CDCl₃, 300 MHz): δ 9.41 (s, 1H), 8.76-8.65 (m, 1H), 8.56-8.45 (m, 1H), 8.18-8.10 (m, 1H), 5.43-5.38 (m, 1H), 4.71-4.50 (m, 1H), 4.38-4.32 (m, 1H), 4.07-3.97 (m, 2H), 3.86-3.84 (m, H), 2.52-2.08 (m, 3H), 2.04-1.90 (m, 6H), 1.67-1.60 (m, 2H), 1.41-1.25 (m, 10H), 0.99-0.83 (m, 21H); MS (EI) m/z 597.5 (M)⁺.

EXAMPLE 24

N-pyrazineformyl-L-leucyl-L-leucyl-L-leucine Boronic Acid (6l)

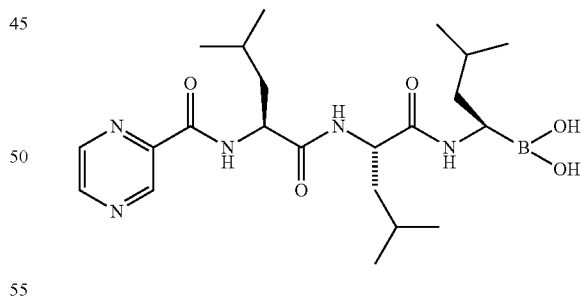

Using the product 5l of Example 23 as a raw material, the synthetic approach and work-up were analogous to that described in Example 2, 14.4 mg of yellow sticky solid was obtained with a yield of 62.8%. ¹H-NMR (CDCl₃, 300 MHz): δ 0.81-0.97 (—CH₃, m, 18H), 1.19~2.82 (—CH₂, —CH, —B(OH)₂, m, 11H), 2.85~2.91 (—CH, m, 1H), 4.53 (—CH, s, 1H), 4.69~4.86 (—CH, m, 1H), 6.99 (—CONH, d, 1H), 7.16 (—CONH, d, 1H), 8.06~8.28 (—CONH, m, 1H), 8.50 (-Pyz, s, 1H), 8.71 (-Pyz, s, 1H), 9.30 (-Pyz, s, 1H); MS (ESI) Measured value m/z 462.3825 (M–H), Calculated value 463.2966.

EXAMPLE 25

Pinanediol N-pyrazineformyl-L-naphthylalanyl-L-leucyl-L-leucine Borate (5m)

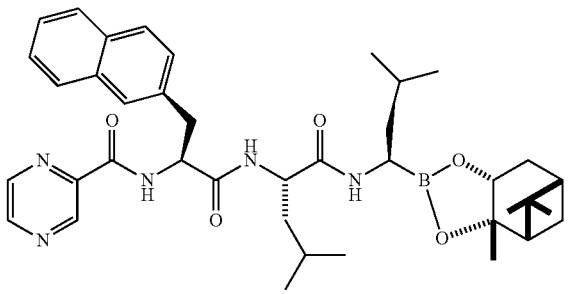

Using the product of Preparation example 36 as a raw material, the synthesis and work-up method were analogous to that described in Example 1, and a white solid was obtained with a yield of 81%. m.p.: 99-100° C. $^1$H-NMR (CDCl$_3$, 300 MHz): δ 9.31 (s, 1H), 8.73 (s, 1H), 8.49 (d, J=1.8 Hz, 1H), 8.33 (d, J=7.5 Hz, 1H), 7.66-7.58 (m, 4H), 7.44-7.38 (m, 3H), 6.48-6.36 (m, 2H), 4.94-4.85 (m, 1H), 4.42-4.30 (m, 1H), 4.25-4.16 (m, 1H), 3.39-3.37 (d, J=6.3 Hz, 2H), 3.19-3.11 (m, 1H), 2.35-2.27 (m, 1H), 2.20-2.15 (m, 1H), 1.89-1.84 (m, 2H), 1.68-1.61 (m, 2H), 1.37-1.36 (m, 3H), 1.53-1.43 (m, 4H), 1.28-1.21 (m, 3H), 0.94-0.89 (m, 6H), 0.83-0.79 (m, 9H); $^{13}$C-NMR (CDCl$_3$, 75 MHz): 171.81, 170.10, 163.298, 147.59, 144.34, 143.72, 142.77, 133.46, 132.47, 128.56, 128.12, 127.62, 127.16, 126.18, 125.80, 85.60, 54.70, 54.53, 51.40, 51.20, 50.96, 40.89, 40.08, 39.85, 39.56, 38.18, 38.09, 35.58, 28.59, 27.08, 26.25, 25.26, 25.46, 24.51, 24.03, 23.00, 22.71, 22.15, 21.94; HRMS Calculated value $_{39}$H$_{53}$BN$_5$O$_5$ (M+1)$^+$ 682.4134, Measured value 682.4152.

EXAMPLE 26

N-pyrazineformyl-L-naphthylalanyl-L-leucyl-L-leucine Boronic Acid (6m)

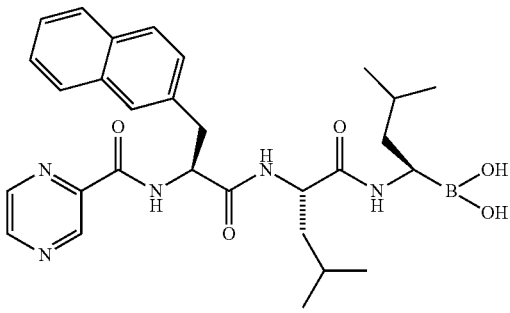 [SMILES: CC(C)C[C@H](NC(=O)[C@H](CC(C)C)NC(=O)[C@H](Cc1ccc2ccccc2c1)NC(=O)c1cnccn1)B(O)O]

Using the product 5m of Example 25 as a raw material, the synthetic approach and work-up were analogous to that described in Example 4, and a milk-white solid was obtained with a yield of 66%. $^1$H-NMR (CDCl$_3$, 300M): δ 9.29 (s, 1H), 8.70 (d, J=2.1 Hz, 1H), 8.45 (d, J=1.8 Hz, 1H), 8.40 (d, J=7.5 Hz, 1H), 7.74-7.66 (m, 4H), 7.45-7.42 (m, 3H), 7.37 (d, J=8.7 Hz, 1H), 5.05-4.93 (m, 1H), 4.53-4.45 (m, 1H), 3.38 (d, J=8.7 Hz, 2H), 2.98-2.83 (m, 1H), 1.99 (s, br, 2H), 1.80-1.51 (m, 1H), 1.50-1.29 (m, 6H), 0.86-0.74 (m, 12H); $^{13}$C-NMR (CDCl$_3$, 75 MHz): 170.59, 170.45, 163.83, 147.74, 144.27, 143.61, 142.77, 133.46, 133.27, 132.47, 128.59, 128.12, 127.63, 127.05, 126.24, 125.84, 54.76, 39.88, 37.74, 25.78, 24.61, 24.48, 23.03, 22.82, 22.63, 21.60, 21.45. MS (ESI) Measured value m/z 462.3825 (M–H), Calculated value 463.2966.

TEST EXAMPLE 1

The Inhibitory Effects of Tripeptide Boronic Acid or Boronic Ester Compounds on the Proteasome The activities of the proteasome were assayed using fluorescent peptides: Suc-leu-leu-Val-Tyr-AMC (Suc represents succinyl, and AMC represents 7-amino-4-methylcoumarin, purchased from SIGMA) for determining chymotryptic-like (CT-L) activity; Z-Ala-Arg-Arg-AMC (Z represents benzyloxycarbonyl, purchased from Calbiochem) for determining trypsin-like (TL) activity; and Z-leu-leu-Glu-βNA (βNA represents β-naphtylamide, purchased from SIGMA) for determining peptidyl-glutamyl-peptide-hydrolyzing (PGPH) enzyme activity.

Method for the aforesaid activity assays is as follows: 1 μg of 20S proteasome extracted from rat liver was incubated with a 100 μL solution containing various concentrations of compounds, 50 μM fluorescent peptides and 20 mM Tris-HCl at 37° C. for 1 h, respectively. The fluorescence released from AMC and RNA reagents was measured by a spectrofluorimeter Fluostar OPTIMA and BMG Germany at excitation/emission wavelengths of 380/440 nm and 335/410 nm, respectively. 0.1% DMSO was used as a solvent control. Compared with the fluorescence of solvent control, an inhibition rate was calculated. Said assays used anticancer drug bortezomib (leukemia drug), namely PS341 as compound for positive control. The results are shown in Table 1.

Table 1 the Inhibitory Effects of Compounds in the Present Invention on the Proteasome

| Compounds No. | CT-L (IC$_{50}$, nM) | T-L (IC$_{50}$, nM) | PGPH (IC$_{50}$, nM) |
| --- | --- | --- | --- |
| PS341 | 0.161 ± 0.024 | >20 | |
| 5a | 0.402 ± 0.024 | >20 | 8.330 ± 2.493 |
| 6a | 0.546 ± 0.077 | >20 | 10.907 ± 3.206 |
| 5b | 0.220 ± 0.106 | >20 | >20 |
| 6b | 0.417 ± 0.070 | >20 | 4.428 ± 1.407 |
| 5c | 0.335 ± 0.031 | >20 | 5.390 ± 0.368 |
| 6c | 0.395 ± 0.035 | >20 | 4.013 ± 1.472 |
| 5d | 0.295 ± 0.049 | >20 | 4.763 ± 1.308 |
| 6d | 0.263 ± 0.081 | >20 | 2.500 ± 1.485 |
| 5e | 0.431 ± 0.086 | >20 | 3.405 ± 0.021 |
| 6e | 0.190 ± 0.017 | >20 | 5.143 ± 2.166 |
| 5f | 0.370 ± 0.141 | >20 | 3.910 ± 1.718 |
| 6f | 0.079 ± 0.011 | >20 | 3.630 ± 1.669 |
| 5g | 0.443 ± 0.081 | >20 | |
| 6g | 0.111 ± 0.050 | >20 | 3.797 ± 0.983 |
| 5h | 0.495 ± 0.092 | >20 | |
| 6h | 0.335 ± 0.078 | >20 | |
| 5i | >20 | >20 | >20 |
| 6i | >20 | >20 | >20 |
| 5j | >20 | >20 | >20 |
| 6j | >20 | >20 | >20 |
| 5k | 0.287 ± 0.019 | >20 | 2.725 ± 1.039 |
| 6k | 0.173 ± 0.033 | >20 | 5.663 ± 0.839 |
| 5l | >20 | >20 | >20 |
| 6l | >20 | >20 | >20 |
| 5m | 0.345 ± 0.106 | >20 | |
| 6m | 0.220 ± 0.070 | >20 | 8.330 ± 2.493 |

TEST EXAMPLE 2

The Preliminary Screening Tests of Anti-Tumor Activities In Vitro

The test methods used in this test example is the routine method for anti-tumor activities test in pharmaceutical area, for example, referring to the following reference: (*J. Immunol Method*, 1983, 65, 55).

Test models: A: MTT method (HL-60 human leukemia); B: SRB method (BGC-823 human gastric cancer); C: SRB method (Bel-7402 human hepatocarcinoma); D: SRB method (KB human nasopharyngeal carcinoma).

The aforesaid tests were carried out with the compounds of Examples 1-26 in the present invention, test results are shown in Tables 2-5. Wherein the test results are indicated as follows: "+++" indicates that inhibition rates at three doses are greater than 50%; "++" indicates that inhibition rates at two doses are greater than 50%; "+" indicates that inhibition rate at one dose is greater than 50%.

Table 2 the Inhibitory Activities on Growth of HL-60 Human Leukemia Cell (MTT Method)

| Compounds No. | Test effects at different doses (Inhibition rate %) | | | results |
|---|---|---|---|---|
| | 0.05 μM | 0.5 μM | 5 μM | |
| 5b | 21.15 | 88.14 | 88.10 | ++ |
| 6b | 3.58 | 87.34 | 88.89 | ++ |
| 5c | −10.46 | 1.94 | 98.97 | + |
| 6c | −16.15 | −8.48 | 64.97 | + |
| 5d | −11.79 | 35.94 | 88.92 | + |
| 6d | −21.09 | −5.04 | 87.91 | + |
| 5f | −19.90 | 81.94 | 88.57 | ++ |
| 6f | 1.26 | 87.39 | 88.63 | ++ |
| 5g | −5.06 | 87.48 | 88.32 | ++ |
| 6g | 5.68 | 87.79 | 88.60 | ++ |
| 5h | 11.38 | 85.54 | 88.26 | ++ |
| 6h | 13.58 | 85.65 | 88.32 | ++ |
| 5m | 11.22 | 82.73 | 87.93 | ++ |
| 6m | 4.61 | 85.20 | 87.79 | ++ |

Table 3 the Inhibitory Activities on Growth of BGC-823 Human Gastric Cancer Cell (SRB method)

| Compounds No. | Test effects at different doses (Inhibition rate %) | | | results |
|---|---|---|---|---|
| | 0.05 μM | 0.5 μM | 5 μM | |
| 5b | 68.59 | 94.76 | 96.54 | +++ |
| 6b | 56.35 | 93.69 | 96.69 | +++ |
| 5c | 3.19 | 55.99 | 96.09 | ++ |
| 6c | 2.64 | 25.10 | 97.70 | + |
| 5d | 23.64 | 93.63 | 97.85 | ++ |
| 6d | 4.33 | 46.66 | 97.55 | + |
| 5f | 38.27 | 89.15 | 83.02 | ++ |
| 6f | 80.30 | 95.52 | 96.79 | +++ |
| 5g | 77.62 | 95.43 | 95.89 | +++ |
| 6g | 76.86 | 95.55 | 97.09 | +++ |
| 5h | 55.00 | 88.97 | 95.40 | +++ |
| 6h | 44.94 | 88.06 | 97.58 | ++ |
| 5m | 45.97 | 84.53 | 97.18 | ++ |
| 6m | 60.31 | 81.93 | 96.99 | +++ |

Table 4 the Inhibitory Activities on Growth of Bel-7402 Human Hepatocarcinoma Cell (SRB method)

| Compounds No. | Test effects under different doses (Inhibition rate %) | | | results |
|---|---|---|---|---|
| | 0.05 μM | 0.5 μM | 5 μM | |
| 5b | 35.88 | 66.68 | 91.05 | ++ |
| 6b | 22.91 | 56.08 | 91.61 | + |
| 5c | 4.18 | 16.63 | 91.12 | + |
| 6c | −2.64 | −4.84 | 71.23 | + |
| 5d | 5.52 | 51.96 | 93.13 | ++ |
| 6d | 1.70 | 8.79 | 90.00 | + |
| 5f | 3.18 | 83.87 | 92.31 | ++ |
| 6f | 39.40 | 90.64 | 93.67 | ++ |
| 5g | 46.67 | 77.65 | 94.73 | ++ |
| 6g | 37.88 | 72.16 | 93.36 | ++ |
| 5h | 13.09 | 51.67 | 90.97 | ++ |
| 6h | 6.61 | 49.76 | 94.80 | + |
| 5m | 6.49 | 52.60 | 95.73 | ++ |
| 6m | 30.30 | 57.72 | 95.23 | ++ |

Table 5 the Inhibitory Activities on Growth of Kb Human Nasopharyngeal Carcinoma Cell (SRB method)

| Compounds No. | Test effects under different doses (Inhibition rate %) | | | results |
|---|---|---|---|---|
| | 0.05 μM | 0.5 μM | 5 μM | |
| 5b | 40.35 | 95.06 | 95.78 | ++ |
| 6b | 23.33 | 91.47 | 96.64 | ++ |
| 5c | 1.84 | 29.83 | 91.36 | + |
| 6c | −13.57 | −5.16 | 95.40 | + |
| 5d | 0.83 | 73.23 | 94.76 | ++ |
| 6d | 3.23 | 17.34 | 96.20 | + |
| 5f | 3.74 | 93.41 | 95.26 | ++ |
| 6f | 32.11 | 95.69 | 97.80 | ++ |
| 5g | 62.79 | 95.50 | 96.51 | +++ |
| 6g | 59.43 | 95.97 | 96.66 | +++ |
| 5h | 20.83 | 91.25 | 94.62 | ++ |
| 6h | 14.25 | 91.77 | 97.40 | ++ |
| 5m | 8.59 | 85.61 | 96.17 | ++ |
| 6m | 40.84 | 86.42 | 94.69 | ++ |

The above test data indicate: (1) the tripeptide boronic acids or boronic esters of the present invention have favorable in vitro anti-tumor activities. The inhibition rates of most of the compounds are larger than 90% at a concentration of 5 μM, and the inhibition rates of some compounds can still be larger than 50.0% even at a concentration of 0.05 μM; (2) the activities are hardly influenced whether the protecting group pinanediol is removed or not.

TEST EXAMPLE 3 in vitro Anti-Tumor Activity ($IC_{50}$)

According to the results of aforementioned preliminary anti-tumor activities screening tests, those compounds which have better anti-tumor activities were selected to measure their $IC_{50}$ values on four types of tumor cell lines: HL-60 (promyelocytic leukemia cell strain), BXPC-3 (human pancreatic cancer cell strain), U266 (multiple myeloma cell strain) and BGC-823 (human gastric carcinoma cell strain). HL-60, BXPC-3 and U266 were obtained from the American Type Culture Collection (Manassas, Va.), and BGC-823 (human gastric carcinoma cell strain) was obtained from China Pharmaceutical University.

Test methods: HL-60 cells were cultured in IMDM medium containing 20% fetal bovine serum at 37° C. in 5% $CO_2$; BGC-823 cells and BXPC-3 cells were cultured in RPMI1640 medium containing 10% fetal bovine serum at 37° C. in 5% $CO_2$; U266 cells were cultured in RPMI1640 medium containing 15% fetal bovine serum at 37° C. in 5% $CO_2$.

The cell growth was measured by the standard MTT method. A dispersions (150 μL, containing 3000 cells) medium was added into each well of a 96-well plate and allowed to grow, after 24 h, ten kinds of medium (50 μL) containing different concentrations of drugs were added into the corresponding wells, and continued to incubate for 72 h. Then a solution containing 5 mg/ml MTT (20 μL) was added into each well and incubated for another 4 h at 37° C. The plate was then centrifugated at 1000 rpm at 4° C. for 5 min, and the medium in upper layer was carefully discarded. The precipitates were dissolved in 100 μL of DMSO, and absorbance was read with an Infinite M200 (Tecan, Austria) microplate reader at 540 nm.

The result was expressed as $IC_{50}$ value, which is the average value of three independent determinations. And the results were shown in Table 6.

TABLE 6

$IC_{50}$ values of some compounds

| Compounds No. | BGC-823 (μM) | BXPC-3 (nM) | HL-60 (nM) | U266 (nM) |
|---|---|---|---|---|
| PS341 | 2.89 | 11.8 | 6.9 | 12.2 |
| 6b | 2.81 | 31.8 | 10 | 53.0 |
| 6c | 5.14 | 445.0 | 552.5 | 250.0 |
| 6d | 2.46 | 256.7 | 444.7 | 66.2 |
| 6f | 0.60 | 21.2 | 4.6 | 9.9 |
| 6g | 1.04 | 28.7 | 7.4 | 15.8 |
| 6h | 2.45 | 33.3 | 19.6 | 195.0 |
| 6m | 1.72 | 43.5 | 15.0 | 120.0 |

As indicated in the results, most of the compounds exhibit better selectivity than that of PS341, and the activities thereof on some tumor strains were apparently higher than that of PS341. For example, the inhibition rates of all these compounds except 6c on the growth of BGC-823 cell were better than that of PS341; and the inhibition rates of 6f on the growth of three types of cells were better than those of PS341.

TEST EXAMPLE 4 in vivo Anti-Tumor Activity

Animal: ICR mice, half male and half female (18-22 g), provided by Laboratory Animal Science Department of Peking Medical University.

Tumor cell strain: murine H22 cells were provided by cell bank of pharmacological group of the State Key Laboratory of Natural and Biomimetic Drugs.

Method: Murine tumor cells were taken to be treated, and diluted to $5 \times 10^6$ cells/ml after treatment. The diluted tumor cells solution was inoculated to the left forelimb oxter of the mice with 0.2 ml/mouse under aseptic condition. 24 h after inoculation, the mice were divided into groups and orally administered once per day to the mice in each group for 10 days. At the 12th day, the tumors were peeled off and weighed, and the average weight of the tumor, standard deviation (SD) and p-value of each group were calculated.

Table 7 in vivo Anti-Tumor Activity of the Compounds 6f and 6m

| Group | Dose (mg/kg) | Animal numbers Start/End | Body weight (g) (X ± SD) | Tumor weight (g) (X ± SD) | Inhibition rate (%) |
|---|---|---|---|---|---|
| NS | / | 8/8 | 6.52 ± 3.06 | 1.25 ± 0.32 | / |
| PS341 | 1 | 8/4 | 0.65 ± 2.07 | 0.47 ± 0.20*** | 62.05 |
| 6f | 1 | 8/6 | 1.49 ± 1.07 | 0.60 ± 0.16*** | 51.67 |
|  | 2 | 8/5 | 0.04 ± 4.29 | 0.56 ± 0.17*** | 55.34 |
| 6g | 1 | 8/8 | −1.28 ± 2.83 | 0.82 ± 0.36* | 34.24 |
|  | 2 | 8/8 | −0.53 ± 2.58 | 0.54 ± 0.28*** | 56.33 |

NS: Blank group;
***P < 0.001;
*P < 0.05

The above test results of in vivo anti-tumor activity assay indicate that the activity of the tripeptide boronic acid of the present invention is comparable to that of bortezomib (PS341), but the compounds of the present invention have obviously reduced toxicity, especially the toxicity of the compound 6g is even lower, thus the compound 6g has a potential to be developed into a proteasome inhibitor with better activity, less toxicity and side effects.

The embodiments of the present invention has been described in details, it is obviously that a lot of modifications and changes can be made by the skilled in the art without deviating from the basic spirit of the present invention. All of these changes and modifications are considered to be within the scope of the present invention.

The invention claimed is:

1. A tripeptide boronic acid compound represented by the following general formula (I):

wherein, $R_1$ is benzyl, $R_2$ is selected from p-hydroxybenzyl, β-indylmethyl, isobutyl or 2-naphthylmethyl, $R_3$ is selected from benzyl, p-hydroxybenzyl, β-indylmethyl, isobutyl or 2-naphthylmethyl and E is H or 2,3-pinanediol ester group.

2. The compound according to claim 1, wherein the $R_3$ group is isobutyl.

3. The compound according to claim 1 wherein the compound is selected from the group consisting of:
Pinanediol N-pyrazineformyl-L-phenylalanyl-L-tyrosyl-L-leucine borate;
Pinanediol N-pyrazineformyl-L-phenylalanyl-L-naphthylalanyl-L-leucine borate;
Pinanediol N-pyrazineformyl-L-phenylalanyl-L-tryptophyl-L-leucine borate;
Pinanediol N-pyrazineformyl-L-phenylalanyl-L-leucyl-L-leucine borate;
N-pyrazineformyl-L-phenylalanyl-L-tyrosyl-L-leucine boronic acid;
N-pyrazineformyl-L-phenylalanyl-L-naphthylalanyl-L-leucine boronic acid;
N-pyrazineformyl-L-phenylalanyl-L-tryptophyl-L-leucine boronic acid; and
N-pyrazineformyl-L-phenylalanyl-L-leucyl-L-leucine boronic acid.

4. A pharmaceutical composition containing a therapeutically-effective amount of a tripeptide boronic acid according to any one of claims 1, 2 and 3 as an active ingredient, and optionally one or more kinds of pharmaceutical carrier(s).

5. The pharmaceutical composition according to claim 4, wherein the content of the active ingredient in the pharmaceutical composition is 0.5%-99%, and the content of the pharmaceutical carrier(s) is 1%-99.5%.

6. The pharmaceutical composition according to claim 5, wherein the composition is formulated into a form for oral administration or a form for parenteral administration, and the form for parenteral administration includes the forms for injection administration, topical administration, inhalation administration, rectal administration or implantable administration.

7. The pharmaceutical composition according to claim 6, wherein the form for oral administration is tablets, capsules, granules or liquid preparations suitable for oral administration, or sustained-release or quantitative release form; and the form for injection administration is injections, freeze-dried powder injections or solutions suitable for infusion.

8. The pharmaceutical composition according to claim 4 for use in preparation of a proteasome inhibitor.

9. A tripeptide boronic acid compound represented by the following general formula (I):

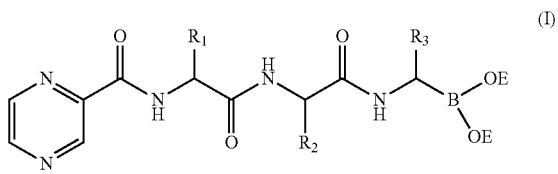

wherein, $R_1$ is selected from p-hydroxybenzyl, β-indylmethyl, isobutyl or 2-naphthylmethyl, $R_2$ is benzyl, p-hydroxybenzyl, β-indylmethyl, isobutyl or 2-naphthylmethyl, $R_3$ is selected from benzyl, p-hydroxybenzyl, β-indylmethyl, isobutyl or 2-naphthylmethyl, and E is H or 2,3-pinanediol ester group.

10. The compound according to claim 9, wherein the R3 group is isobutyl.

11. The compound according to claim 10 wherein the compound is selected from the group consisting of:
Pinanediol N-pyrazineformyl-L-naphthylalanyl-L-phenylalanyl-L-leucine borate;
Pinanediol N-pyrazineformyl-L-tyrosyl-L-phenylalanyl-L-leucine borate;
Pinanediol N-pyrazineformyl-L-leucyl-L-phenylalanyl-L-leucine borate;
Pinanediol N-pyrazineformyl-L-leucyl-L-naphthylalanyl-L-leucine borate;
Pinanediol N-pyrazineformyl-L-naphthylalanyl-L-naphthylalanyl-L-leucine borate;
Pinanediol N-pyrazineformyl-L-tryptophyl-L-phenylalanyl-L-leucine borate;
Pinanediol N-pyrazineformyl-L-leucyl-L-leucyl-L-leucine borate;
Pinanediol N-pyrazineformyl-L-naphthylalanyl-L-leucyl-L-leucine borate;
N-pyrazineformyl-L-naphthylalanyl-L-phenylalanyl-L-leucine boronic acid;
N-pyrazineformyl-L-tyrosyl-L-phenylalanyl-L-leucine boronic acid;
N-pyrazineformyl-L-leucyl-L-phenylalanyl-L-leucine boronic acid;
N-pyrazineformyl-L-leucyl-L-naphthylalanyl-L-leucine boronic acid;
N-pyrazineformyl-L-naphthylalanyl-L-naphthylalanyl-L-leucine boronic acid;
N-pyrazineformyl-L-tryptophyl-L-phenylalanyl-L-leucine boronic acid;
N-pyrazineformyl-L-leucyl-L-leucyl-L-leucine boronic acid; and
N-pyrazineformyl-L-naphthylalanyl-L-leucyl-L-leucine boronic acid.

12. A pharmaceutical composition containing a therapeutically-effective amount of a tripeptide boronic acid according to claim 9 as an active ingredient, and optionally one or more kinds of pharmaceutical carrier(s).

13. The pharmaceutical composition according to claim 12, wherein the content of the active ingredient in the pharmaceutical composition is 0.5%-99%, and the content of the pharmaceutical carrier(s) is 1%-99.5%.

14. The pharmaceutical composition according to claim 13, wherein the composition is formulated into a form for oral administration or a form for parenteral administration, and the form for parenteral administration includes the forms for injection administration, topical administration, inhalation administration, rectal administration or implantable administration.

15. The pharmaceutical composition according to claim 14, wherein the form for oral administration is tablets, capsules, granules or liquid preparations suitable for oral administration, or sustained-release or quantitative release form; and the form for injection administration is injections, freeze-dried powder injections or solutions suitable for infusion.

16. The pharmaceutical composition according to claim 12 for use in preparation of a proteasome inhibitor.

* * * * *